United States Patent
Kharazi et al.

(10) Patent No.: US 8,105,380 B2
(45) Date of Patent: Jan. 31, 2012

(54) CELLULAR SCAFFOLD

(75) Inventors: Alexander Kharazi, San Diego, CA (US); Ludmila Kharazi, San Diego, CA (US)

(73) Assignee: Stemedica Cell Technologies, Inc., San Diego, CA (US)

(*) Notice: Subject to any disclaimer, the term of this patent is extended or adjusted under 35 U.S.C. 154(b) by 603 days.

(21) Appl. No.: 11/616,787

(22) Filed: Dec. 27, 2006

(65) Prior Publication Data

US 2008/0095748 A1 Apr. 24, 2008

Related U.S. Application Data

(60) Provisional application No. 60/854,059, filed on Oct. 23, 2006.

(51) Int. Cl.
*A61F 2/10* (2006.01)

(52) U.S. Cl. ...................... 623/15.12; 435/395

(58) Field of Classification Search ................ None
See application file for complete search history.

(56) References Cited

U.S. PATENT DOCUMENTS

| | | | |
|---|---|---|---|
| 5,147,401 A | 9/1992 | Bakker | |
| 5,282,859 A | 2/1994 | Eisenberg | |
| 5,460,939 A | 10/1995 | Hansbrough | |
| 5,489,304 A | 2/1996 | Orgill | |
| 5,667,961 A | 9/1997 | Bernard | |
| 5,693,332 A * | 12/1997 | Hansbrough | 424/426 |
| 5,695,996 A | 12/1997 | Quinn | |
| 5,716,411 A | 2/1998 | Orgill | |
| 5,858,721 A | 1/1999 | Naughton | |
| 6,039,760 A | 3/2000 | Eisenberg | |
| 6,051,425 A * | 4/2000 | Morota et al. | 435/325 |
| 6,110,208 A | 8/2000 | Soranzo | |
| 6,471,958 B2 | 10/2002 | Dimitrijevich | |
| 6,497,875 B1 | 12/2002 | Sorrell | |
| 6,500,464 B2 | 12/2002 | Ceres | |
| 6,638,709 B2 | 10/2003 | Tai | |
| 6,733,530 B1 | 5/2004 | Lam | |
| 6,815,202 B2 | 11/2004 | Hoeffler | |
| 6,962,814 B2 | 11/2005 | Mitchell | |
| 6,964,869 B2 | 11/2005 | Allen-Hoffmann | |
| 7,041,868 B2 | 5/2006 | Greene | |
| 2002/0082692 A1 | 6/2002 | van Blitterswijk | |
| 2002/0172705 A1 | 11/2002 | Murphy | |
| 2003/0109920 A1 | 6/2003 | Martins-Green | |
| 2004/0028657 A1 | 2/2004 | Okano | |
| 2004/0162615 A1 | 8/2004 | Lam | |

(Continued)

FOREIGN PATENT DOCUMENTS

EP 1375647 1/2004

(Continued)

OTHER PUBLICATIONS van den Bogaerdt et al, Wound Repair and Regeneration, 2004, vol. 12, pp. 225-234.*

(Continued)

*Primary Examiner* — Allison Ford
(74) *Attorney, Agent, or Firm* — Timothy M. Brown

(57) ABSTRACT

A cellular scaffold that is suitable for tissue regeneration, cell culture and in vitro assays. The invention relates to a layered cell scaffold that is seeded with mesenchymal and ectodermal cells. The layered cellular scaffold comprises an inoculum of mesenchymal cells and ectodermal cells positioned between two opposing scaffolds in a sandwich configuration. The layered cell scaffold provides a functional skin equivalent that is suitable for transplantation and in vitro cell-based assays.

28 Claims, 5 Drawing Sheets

U.S. PATENT DOCUMENTS

2004/0171145 A1 9/2004 Jorcano
2005/0107876 A1 5/2005 Kim

FOREIGN PATENT DOCUMENTS

| WO | WO9741208 | 11/1997 |
| WO | WO0246375 | 6/2002 |
| WO | WO2006018147 | 2/2006 |

OTHER PUBLICATIONS

Lamme et al, Journal of Investigative Dermatology, 1998, vol. 111, pp. 989-995.*
Yannas; Wound Tissue Can Utilize a Polymeric Template to Synthesize a Functional Extension of Skin; Science; Jan. 8, 1982; 174-176; vol. 205; USA.

* cited by examiner

| | |
|---|---|
| Fibroblasts $1 \times 10^5$ cells per well. CnT-05 medium<br><br>Results: Cells in good condition | Fibroblasts on Spongostan $1 \times 10^5$ cells CnT-05<br><br>Results: No lysis of Spongostan |
| Fibroblasts $1 \times 10^5$ cells per well. CnT-05 medium<br><br>Results: Cells in good condition | Fibroblasts on Spongostan $1 \times 10^5$ cells CnT-05<br><br>Results: No lysis of Spongostan |

| Keratinocytes $1\times10^5$ cells PCT medium | Keratinocytes on Spongostan $1\times10^5$ cells PCT medium | Keratinocytes on Spongostan + FIB-cap PCT medium SANDWICH (face to face) | Keratinocytes on Spongostan + spongostan-cap PCT medium $1\times10^5$ cells SANDWICH (face to face) |
|---|---|---|---|
| Result: Cells in good condition | Result: Lysis of spongostan | Result: NO LYSIS | Result: Lysis of spongostan |
| Keratinocytes $1\times10^5$ cells PCT medium | Keratinocytes on Spongostan $1\times10^5$ cells PCT medium | Keratinocytes on Spongostan + FIB-cap PCT medium SANDWICH (face to face) | Keratinocytes on Spongostan + FIB PCTsupernatant PCT medium $1\times10^5$ cells |
| Result: Cells in good condition | Result: Lysis of spongostan | Result: NO LYSIS | Result: Lysis of spongostan |

Fig. 3

Fig. 4

CELLULAR SCAFFOLD

CROSS-REFERENCE TO RELATED APPLICATION

This application claims priority from U.S. Provisional Patent Application Ser. No. 60/854,059, filed Oct. 23, 2006 and entitled, "Cellular Scaffold," which is incorporated by reference in its entirety.

FIELD OF THE INVENTION

The present invention generally relates to tissue engineering and specifically relates to scaffolding for cell and tissue culture. Particularly, the invention relates to a cellular scaffold that is seeded with regenerative cells. More particularly, the invention relates to a layered cellular scaffold that has ectodermal cells and mesenchymal cells seeded between at least two biocompatible substrates. The invention also relates to methods of using a layered scaffold for cell transplantation, cell culture and cell-based in vitro assays.

BACKGROUND

The tissue engineering field is advanced and a variety of tissue equivalents have been developed. Not only do these equivalents vary in the material that is used as a scaffold, they also vary in the type and source of cells which are seeded on the scaffold. Skin equivalents are one area of tissue engineering that has witnessed significant research and commercial development.

Modern skin equivalents may be made using a variety of materials and methods. For example, a cultured skin may be prepared by culturing human fibroblasts in collagen gel, followed by inoculating and culturing human keratinocytes on the gel after the gel has shrunk (U.S. Pat. No. 4,485,096). Another skin equivalent is prepared by inoculating and culturing human fibroblasts on nylon mesh, followed by inoculating and culturing human keratinocytes thereon when the pores of the mesh are filled up with secreted materials from the fibroblasts (Slivka, S. R., L. Landeen, Zimber, M., G. K. Naughton and R. L. Bartel, J. Invest. Dermatol., 96: 544A, 1991). Alternatively, a skin may be prepared by inoculating and culturing human fibroblasts on a collagen sponge, followed by a laminating collagen gel or film that is inoculated with human keratinocytes thereon (J. Jpn. P. R. S., 10, 165-180 (1990) and Japanese Examined Patent Publication No. 47043/1995).

The advanced nature of skin equivalents is demonstrated by the fact that a number of skin equivalents are commercially available. Commercial skin equivalents include EpiCel™ (which lacks a dermal component and uses the patient's own cultured keratinocytes) Integra™ (which uses a collagen-glycosaminoglycan (GAG) matrix to provide an acellular dermal component and uses a thin epidermal autograft), Allo-Derm™, (which uses a dermal matrix and a thin epidermal autograft), DermaGraft™ (which uses a polyglycolic acid/polylactic acid (PGA/PLA) matrix and allogeneic human fibroblasts for the dermis), Hyaff/LaserSkin™ (which uses hyaluran and fibroblasts for the dermis, and hyaluran and the patient's own keratinocytes for the epidermis), and PolyActive™ (which uses polyethylene oxide/polybutylthalate (PEO/PBT) and the patient's own fibroblasts for the dermis, and the patient's own cultured keratinocytes for the epidermis).

Other commercially available skin equivalents include ApliGraft™, which uses collagen gel and allogeneic fibroblasts for the dermis, and cultured allogeneic keratinocytes for the epidermis, Comp Cult Skin™ or OrCel™, which uses collagen and allogeneic fibroblasts for the dermis, and cultured allogeneic keratinocytes for the epidermis, and TransCyte™, which uses allogeneic fibroblasts for the dermis and a synthetic material, BioBrane™, for the epidermis.

Skin equivalents have been used to treat a variety of skin defects. Successful regeneration of skin has been observed for injuries such as burns and skin disorders that result from a disease such as diabetic ulcers. The use of cellular scaffolds (i.e. skin equivalents) is not limited to therapeutic tissue regeneration as they are also applied to cell-based assays and tissue culture systems.

The production of therapeutic tissue models using fibroblasts in combination with other cells, such as epidermal keratinocytes presents certain challenges. For example, although fibroblasts provide growth factors and other cell-to-cell contacts that facilitate cell division, their proliferation may outpace epidermal cell division resulting in a culture that is overgrown with fibroblasts. This is clearly undesirable as therapies aimed at the regeneration of epidermal tissues must be carried out using carriers rich in epidermal cells. One means of preventing the overgrowth of fibroblasts involves plating the epidermal cells with irradiated 3T3 (mouse) fibroblast cells (Rheinwald and Green, Cell, 6, 331-334, November 1975). However this technique requires the presence of dermal components which is undesirable in therapeutic applications. Another approach for producing skin equivalents with a high number of keratinocyte precursors is to seed the cell scaffold with more keratinocytes than fibroblasts. However, when precursor keratinocytes are cultured without fibroblasts, they produce greater levels of collagenase making the seeding of collagen scaffols with keratinocytes alone impossible.

What is needed in the art therefore is a tissue equivalent having therapeutically appropriate proportions of keratinocyte and fibroblast cells. Also needed in the art is a means for producing a collagenase-inhibited population of keratinocyte stem cells which are capable of being expanded on a collagen scaffold in the absence of fibroblasts.

SUMMARY OF THE INVENTION

The present invention relates to the field of tissue engineering. In particular, the invention relates to a cellular scaffold that is suitable for tissue regeneration, cell culture and in vitro assays. More particularly, the invention relates to a layered cell scaffold that is seeded with mesenchymal cells and ectodermal cells. In a specific embodiment, the mesenchymal cells are fibroblasts and the ectodermal cells are precursor keratinocytes. The layered cell scaffold provides a functional skin equivalent that is suitable for transplantation and in vitro cell-based assays.

An objective of the present invention is to provide a cellular scaffold arrangement comprising a first cell scaffold having a first surface and a second surface wherein said second surface of said first cell scaffold is seeded with mesenchymal cells, and a second cell scaffold having a first surface and a second surface wherein said first surface of said second cell scaffold is seeded with ectodermal cells, wherein said second surface of said first scaffold is in contact with said first surface of said second scaffold. In some embodiments, the ectodermal cells are precursor keratinocytes, and the mesenchymal cells are fibroblasts.

Another objective of the invention is to provide a layered cellular scaffold comprising an first cellular scaffold having a contacting surface that is seeded with ectodermal cells, a second cellular scaffold having a contacting surface that is seeded with mesenchymal cells, and a scaffold interface wherein said first scaffold contacting surface substantially contacts said second scaffold contacting surface. In some embodiments, the ectodermal cells are precursor keratinocytes, and the mesenchymal cells are fibroblasts.

Another objective of the invention is to provide a method of making a layered cellular scaffold comprising providing a first cell substrate having a first surface and a second surface, seeding said second surface of said first cell substrate with mesenchymal cells, providing a second cell substrate having a first surface and a second surface, seeding said first surface of said second cell substrate with mesenchymal cells, and contacting said second surface of said first cell substrate with said first surface of said second cell substrate thereby producing said layered cellular scaffold. In some embodiments, the ectodermal cells are precursor keratinocytes, and the mesenchymal cells are fibroblasts.

Another objective of the invention is to provide a method for making a layered cellular scaffold comprising, providing a first cell scaffold and a second cell scaffold, seeding a surface of said first cell scaffold with mesenchymal cells, seeding a surface of said second cell scaffold with ectodermal cells, and joining said seeded surfaces to create said layered cellular scaffold. In some embodiments, the ectodermal cells are precursor keratinocytes, and the mesenchymal cells are fibroblasts.

Another aspect of the invention concerns a kit for correcting a tissue defect comprising, a first container having therein isolated ectodermal cells in a pharmaceutically acceptable carrier, a second container having therein isolated mesenchymal cells in a pharmaceutically acceptable carrier, and at least one cell scaffold wherein said at least one cell scaffold is suitable for cell culture, wherein said first container, said second container and said cell scaffold are substantially enclosed in a packaging material. In some embodiments, the ectodermal cells are precursor keratinocytes, and the mesenchymal cells are fibroblasts.

Another objective of the invention is to provide a method for seeding a collagen matrix with precursor keratinocytes comprising obtaining a heterogenous cell population from tissue, culturing said heterogenous cell population in PCT medium for at least 6 days, culturing said cultured heterogenous cell population in CMT medium for approximately 24 hours to produce a population of precursor keratinocytes, culturing said population of precursor keratinocytes in calcium-supplemented CMT medium to produce collagenase-inhibited precursor keratinocytes, and seeding said matrix with said collagenase-inhibited precursor keratinocytes.

Another objective of the invention is to provide a method for inhibiting the collagenase activity of precursor keratinocytes comprising providing a primary culture of precursor keratinocytes, culturing said primary culture of precursor keratinocytes in PCT-defined medium for at least 6 days to produce a cultured population of precursor keratinocytes, culturing said cultured population of precursor keratinocytes in calcium-free CMT medium for approximately 24 hours to produce a population of CMT-conditioned precursor keratinocytes, and culturing said population of CMT-conditioned precursor keratinocytes in calcium-supplemented CMT medium,

BRIEF DESCRIPTION OF THE DRAWINGS

FIG. 3 is an abstract representation of eight culture wells from Example 6. The culture wells were seeded under various conditions including culture wells seeded with basal keratinocytes alone, culture wells with basal keratinocytes seeded on Spongostan, and basal keratinocytes seeded on Spongostan in a sandwich configuration with fibroblast-seeded Spongostan. Also presented are the cell growth results observed after culture according to Example 6.

FIGS. 4 and 6 are images of a basal keratinocyte-seeded Spongostan scaffold after the scaffold was rescued from a sandwich configuration. The scaffold was cultured in a sandwich configuration with a fibroblast-seeded scaffold.

DEFINITIONS

Figures 1, 2:
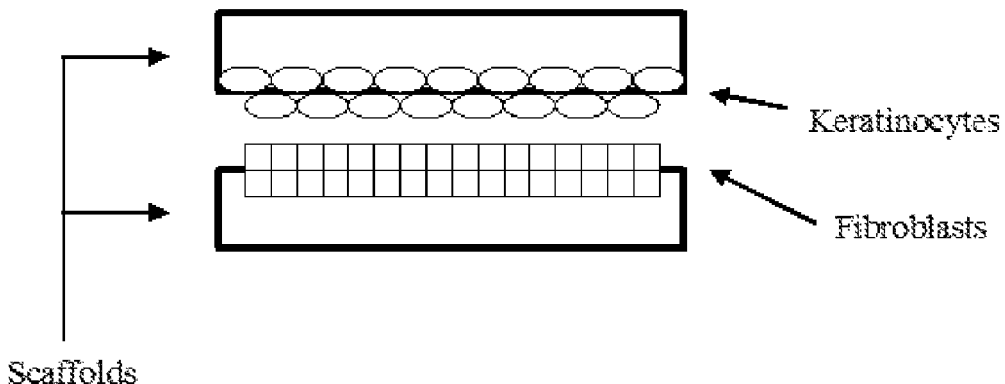
FIG. 1 depicts keratinoctyes and fibroblasts seeded on a pair of scaffolds in a sandwich configuration.
FIG. 2 is an abstract representation of four culture wells from Example 4. The culture wells were seeded with either fibroblasts on Spongostan or fibroblasts alone. Also presented are the cell growth results observed after culture according to Example 4.

The term "matrix" or "scaffold" as used herein refers to a three-dimensional structure upon which the cells disclosed herein are seeded. Embodiments of these scaffolds are permeated by open spaces of a fixed or variable volume. Scaffolds of the invention may take on a variety of consistencies, including, but not limited to, sponges (i.e. foams), gels, and combinations thereof.

The term "cell scaffold" refers to a three-dimensional matrix that is suitable for uses such as cell culture and cell transplantation. The cell scaffolds of the invention are porous structures of a biodedgradable substance having interconnecting pores of a size sufficient for cells to invade the matrix. The cell scaffolds of the invention may be derived from any biologically compatible material including, but not limited to matrices derived from proteins (e.g. collagen), polysaccharides, synthetic polymers, and combinations thereof.

"Cellular scaffold" is used to refer to a cell scaffold that is seeded with cells. Cellular scaffolds may exist as layered or unlayered arrangements. Layered cellular scaffold have layers of one or more biologically compatible substrates that are suitable for cell culture and/or cell transplantation. Cell scaffolds are preferably have opposing first and second planar surfaces which are separated by the matrix material of the scaffold. The planar surfaces of the scaffold may also be described as the upper and lower surfaces of the scaffold.

A "layered cellular scaffold," or "cellular scaffold arrangement," is a composition comprising at least a first cell scaffold and second cell scaffold, in which at least one of the cell scaffolds is seeded with cells on at least one surface. The seeded surface(s) of these scaffolds are juxtaposed to create a single structure having an innoculum of at least one cell type positioned between the opposing scaffolds. The scaffolds may be any shape suitable for the culture and/or implantation of cells. In one aspect of the invention, the seeded scaffolds are planar in shape such that, when joined, they form a sandwich-like structure.

The term "tissue equivalent" is used to describe a cellular scaffold with characteristics similar to a natural tissue such as common physiological functions, cell types and/or structures. A "skin equivalent," for example, could contain an upper cell scaffold that represents the epithelium (e.g. a cell scaffold that is seeded with precursor keratinocytes), and a lower cell scaffold that represents the dermal layer (e.g. a scaffold that is seeded with fibroblasts).

The terms "derive," "derived from" and "derivative," may be used to refer to both cell scaffold materials and cells. When used to refer to a cell scaffold material, "derived from" indicates that the material incorporates a specific substance. When used to refer to a cell, "derived from," indicates that the cell came from a specific source such as, for example, a tissue, a clonal cell line, a body fluid (e.g. umbilical cord blood), or a primary cell culture. For example, when a cell population is expanded from a clonal cell isolated from the ectoderm germ layer, the cell population may be described as being derived from the ectoderm germ layer and/or the clonal cell.

The term "ectoderm" refers to the outermost germ layer of cells derived from the inner cell mass of the blastocyst. Through cell division and specialization, the ectoderm gives rise to the cells which make up the nervous system, sensory organs, skin, and related structures (e.g. sweat glands, hair, and nails). Cells which originate from the ectoderm are said to belong to the ectodermal lineage.

The term "ectodermal cell" refers to any cell of ectodermal lineage. The ectodermal cells of the invention may have varying degrees of potency and differentiation. Ectodermal cells include stem cells (i.e. ectodermal stem cells) which are undifferentiated cells capable of an indefinite number of divisions in culture, and which have the ability to form one or more fully differentiated terminal cells. Precursor keratinocytes are one example of an ectodermal cell. Ectodermal cells also include fully differentiated terminal cells such as keratinocytes and neurons. Precursor keratinocytes are but one example of an ectodermal cell.

The terms "precursor cell," "precursor," "tissue precursor cell" and "progenitor cell" are used interchangeably herein and refer to a lineage-committed cell that divides and differentiates to form new, specialized tissue(s). It should be understood that an "epidermal progenitor cell" is used interchangeably with the terms "progenitor keratinocyte" and "precursor keratinocyte" to denote regenerative cells of the epidermis. Precursor keratinocytes as disclosed herein are regenerative and differentiate into fully differentiated terminal keratinocytes. Precursor keratinocytes are one example of a precursor cell. One source of precursor keratinocytes is the basal layer of the skin which contains the most primitive, i.e. most multipotent, stem cells in the epidermis. Basal keratinocytes, derived from the basal layer of the epidermis (i.e. basal cells), are a form of precursor keratinocyte.

As used herein, the term "differentiate," "differentiation," "differentiated," or "differentiating" means any change in cellular gene expression accompanied by, or accompanying, the restriction of a cell and its progeny to a more specific cell-type lineage. For example, changes in gene expression accompany the differentiation of a keratinocyte from an ectodermal stem cell or the differentiation of an endothelial cell from a bone marrow stem cell.

"Regenerative" is used to refer to the ability of a substance to restore, supplement or otherwise rehabilitate the natural function of a tissue. This ability may be conferred by, for example, treating a dysfunctional tissue with regenerative cells. Regenerative cells treat dysfunctional tissue by either replacing it with new cells capable of performing the tissue's natural function, or by helping to restore the natural activity of the dysfunctional tissue.

"Pluripotent," or "pluripotency" refers to the ability of a single stem cell to give rise to all of the various cell types that make up the body of an animal. Pluripotent cells cannot make so-called "extra-embryonic" tissues such as the amnion, chorion, and other components of the placenta. Pluripotent cells are capable of forming cells belonging to all three germ lineages (i.e. the endodermal, ectodermal and mesodermal lineages).

"Mutlipotent," or "multipotency," refers to the ability of a single stem cell to develop into all the different cell types that originate from a single germ lineage. That is, a multipotent cell is capable of forming all or many of the cells belonging to the endodermal, ectodermal or mesodermal lineages.

A "clone," or "clonal cell," is a line of cells that is genetically identical to the originating cell. This cloned line is produced by cell division (mitosis) of the originating cell. The term "clonal population" in reference to the cells of the invention shall mean a population of cells that is derived from a clone. A cell line may be derived from a clone and is an example of a clonal population.

The term "cell line" refers to a population of cells cultured in vitro that has descended through one or more generations (and possibly cultures) from a single primary culture or a clone.

The mesenchymal cells of the invention are mesodermal lineage cells having varying levels of potency. The potency of the mesenchymal cells ranges from multipotent stem cells capable of forming all cells of mesodermal origin, down to fully differentiated terminal cells that are capable of performing a specific physiological function. Examples of terminal mesenchymal cells include, but are not limited to, fibroblasts, osteoblasts, chondrocytes, myocytes, and adipocytes. The mesenchymal cells of the invention include precursor cells which are capable of forming one or more types of terminal cells. The mesenchymal cells of the invention further include, but are not limited to, multipotent stem cells having the ability to form any type of cell that originates from the mesoderm. The mesenchymal cells of the invention may be derived from sources including umbilical cord blood, placenta, Wharton's jelly, bone marrow and peripheral blood. Mesenchymal cells may also be derived from the in vitro differentiation of pluripotent embryonic stem cells.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

The term "substrate" or "cell substrate" refers to any surface that can be used for the culture or therapeutic application of the cells disclosed herein. A spongiform scaffold made from a porous biocompatible material is an example of a substrate. The term "substrate" includes, but is not limited to, sponges, microbeads (i.e. microcarriers), membranes, gels and combinations thereof. Substrates of the invention may be planar in shape and have opposing planar surfaces which are separated by the substrate material.

The term "sponge," or "foam," refers to any porous, biocompatible material capable of supporting the growth and implantation of the cells disclosed herein. Sponges of the invention may have pores of any size that permit the growth and invasion of mammalian cells in both culture and in vivo. Pore sizes for use with the invention include but are not limited to pores of about $100\pm50$ μm, between about 50 to 300 μm, and about 80 to 120, often about 100 μm. Examples of sponges include, without limitation, gauzes and other porous materials such as foams. The term "spongiform," or "spongy," means resembling a sponge (e.g. an absorbable gelatin sponge), or having a spongelike consistency or texture.

The term "absorbable gelatin sponge" ("AGS") [USP] as used herein refers to a sterile, absorbable, water-insoluble gelatin-based sponge that is commonly used as a local hemostatic. The AGS can be of any desired shape including, but not limited to planar shapes, sac-like shapes, tubular shapes, linear shapes, and combinations thereof. The shape of the AGS is chosen to best correct any physical defect in the patient. Spongostan™ and Gelfoam™ are examples of an absorbable gelatin sponge that are commercially available from Johnson and Johnson and Upjohn respectively.

The term "hydrogel" or "gel" as used herein, refers to a semisolid composition constituting a substantial amount of water, and in which polymers or mixtures thereof are dissolved or dispersed.

As used herein, the term biodegradable describes the ability of a material to be broken down (e.g., degraded, eroded, dissolved) in vivo. The term includes the degradation of a substance with or without elimination from the body (e.g., by bioresorption or bioabsortion). Biodegradable materials (e.g. cell scaffolds) may be absorbed into bodily fluids in vivo, or degraded and ultimately eliminated from the body, either by conversion into other materials or by breakdown and elimination through natural pathways. The term "biodegradable" as used herein denotes a composition that is not biologically harmful. The rate of degradation of biodegradable materials for use with the invention (e.g. cell scaffold materials) may be adjusted to suit specific applications without undue experimentation.

The terms "restore," "restoration" and "correct" are used interchangeably herein and refer to the regrowth, augmentation, supplementation, and/or replacement of a defective tissue with a new and preferentially functional tissue. The terms include the complete and partial restoration of a defective tissue The term "biological activity" as used herein refers to the effect that an agent has on a cell or population of cells. Effects that fall within the scope of this term include, but are not limited to, cytotoxicity, mutagenicity, proliferation, permeability, apoptosis, gene regulation, protein expression, cell cycle regulation, and differentiation. Drug efficacy, or the desired effect of a test agent, is also encompassed by the term "biological activity."

The term "explant" as used herein refers to a collection of cells from an organ, taken from the body of an individual and grown in an artificial medium. When referring to explants from an organ having both stromal and epithelial components, the term generally refers to explants which contain both components in a single explant from that organ.

The terms "epithelia" and "epithelium" refer to the cellular covering of internal and external body surfaces (cutaneous, mucous and serous), including the glands and other structures derived therefrom, e.g., corneal, esophageal, laryngeal, epidermal, hair follicle and urethral epithelial cells. Other exemplary epithelial tissues include: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The epidermis is composed of squamous epithelium cells and provides one example of an epithelial tissue. The term epithelium can also refer to transitional epithelium, which is that characteristically found lining hollow organs, such as the larynx and urethra, that are subject to great mechanical change due to contraction and distention, e.g. tissue which represents a transition between stratified squamous and columnar epithelium. Epithelia originate from epithelial stem cells.

The term "epidermal equivalent" or "skin equivalent" is used to describe an in vitro generated organotypic tissue culture resembling in its histological structure the natural epidermis especially concerning the stratification and development of the horny layer. A normal stratified epidermis consists of a basal layer of small cuboidal cells, several spinous layers of progressively flattened cells, a prominent granular layer and an orthokeratotic horny layer. All these layers can be detected in epidermal equivalents. Localization of those epidermal differentiation products that have been assayed by immunohistochemistry (e.g. keratins, involucrin, filaggrin, integrins) is similar to that found in normal epidermis.

A "test agent" is any substance that is evaluated for its ability to diagnose, cure, mitigate, treat, or prevent disease in a subject, or is intended to alter the structure or function of the body, organ or cells of a subject. Test agents include, but are not limited to, chemical compounds, biologic agents, proteins, peptides, nucleic acids, lipids, polysaccharides, supplements, signals, diagnostic agents and immune modulators. In some aspects of the invention, test agents include electromagnetic and/or mechanical forces.

"Polysaccharides" as used herein refer to complex carbohydrates made of more than one saccharide. Included in the definition are anionic polysaccharides, including non-modified as well as chemical derivatives thereof, that contains one negatively charged group (e.g., carboxyl groups at pH values above about 4.0) and includes salts thereof, such as sodium or potassium salts, alkaline earth metal salts such as calcium or magnesium salts. Non-limiting examples of anionic polysaccharides include pectin, alginate, galactans, galactomannans, glucomannans and polyuronic acids.

A "glycosaminoglycan" or "GAG" as used herein refers to a long unbranched polysaccharide molecules found on the cell surface or extracellular matrix. Non-limiting examples of glycosaminoglycans include heparin, chondroitin sulfate, dextran sulfate, dermatan sulfate, heparan sulfate, keratan sulfate, crosslinked or non-crosslinked hyaluronic acid, hexuronyl hexosaminoglycan sulfate, and inositol hexasulfate. Derivatives, salts and mimetics of the above, including low molecular weight heparin are intended to be included in the invention. Without wishing to be bound to theory, the presence of certain GAGs, in particular heparin, aids in immobilizing heparin binding growth factors such as those of the Fibroblast Growth Factor (FGF) family.

The term "tissue" is used to refer to an aggregation of similarly specialized cells united in the performance of a particular function. Tissue is intended to encompass all types of biological tissue including both hard and soft tissue. A "tissue" is a collection or aggregation of particular cells embedded within its natural matrix, wherein the natural matrix is produced by the particular living cells. The term may also refer to ex vivo aggregations of similarly specialized cells which are expanded in vitro such as artificial organs.

The term "isolated," or "purified" refers to a cell or population of cells which has been separated from its natural environment. This term includes gross physical separation from the cell's natural environment, and alteration of the cell's relationship with the neighboring cells with which it is in direct contact by, for example, dissociation. When used to refer to a population of cells, the term "isolated" includes populations of cells which result from the proliferation of cells which have been taken (i.e. isolated) from an animal. "Isolated" also refers to cells or populations of cells isolated from a tissue preparation by, for example, affinity chromatography and FACS. Populations of isolated cells are about 30%, 35%, 40%, 45%, 50%, 55%, 60%, 65%, 70%, 75%, 80%, 85%, 90%, 95% or 99% free from other undesired, contaminating cells. A clonal cell line, which is free of contaminating cells, is another, non-limiting example of an isolated cell. In some embodiments, isolated stem cells are substantially free of soluble, naturally occurring molecules.

DETAILED DESCRIPTION

The present invention relates to a cellular scaffold, methods for making the cellular scaffold and methods for its use including, tissue regeneration, cell culture and cell-based assays. The cellular scaffold comprises a layered arrangement having a layer of ectodermal cells and a layer of mesenchymal cells sandwiched between at least two biocompatible substrates. More particularly, the invention relates to a cellular scaffold with a layer of precursor keratinocytes and a layer of fibroblasts between at least two opposing cell scaffolds. The invention further relates to methods for producing a population of collagenase-inhibited precursor keratinocytes suitable for seeding collagen scaffolds without the use of a feeder cell layer.

1. Ectodermal Cells

Ectodermal cells for use with the invention may have different levels of potency. The potency of these cells ranges from multipotent ectodermal stem cells which are capable of forming any cell that differentiates from the ectoderm layer, down to terminal, fully differentiated cells such as, for example, a keratinocyte. In one aspect of the invention, the ectodermal cells are of the keratinocyte lineage.

Precursor keratinocytes suitable for use with the invention are present in a variety of tissue compartments including the basal layer of the epidermis, the hair bulge, neonatal foreskin and the corneal limbus (Ghazizadeh, S. "Organization of stem cells and their progeny in human epidermis" J. Invest. Dermatol. (2005) 124(2):367-72; Watt F M. "Epidermal stem cells: markers, patterning and the control of stem cell fate" Philos. Trans. R. Soc. Lond. B. Biol. Sci. (1998) 353(1370): 831-7; Ito, M. "Stem cells in the hair follicle bulge contribute to wound repair but not to homeostasis of epidermis" Nat. Med. (2005) 1(12):1351-1354; Ito, M. "Hair follicle stem cells in the lower bulge form the secondary germ, a biochemically distinct but functionally equivalent progenitor cell population, at the termination of catagen" Differentiation (2004) 72(9-10):548-557; Chee, K.Y. "Limbal stem cells: the search for a marker" Clin. Exper. Opthamol. (2006) 34(1): 64-73; and Webb A "Location and phenotype of human adult keratinocyte stem cells of the skin" Differentiation (2004) 72(8):387-95).

The precursor keratinocytes of the inventive composition may be derived from post-natal and prenatal tissues (see e.g. Zhou, J. X. "Enrichment and identification of human 'fetal' epidermal stem cells" Hum. Reprod. (2004) 19(4):968-74). In addition, the precursor keratinocytes may be autologous, allogeneic or xenogeneic with respect to a recipient when the cellular scaffold is used for therapeutic tissue regeneration.

In one therapeutic application of the invention, the cellular scaffold is seeded with precursor keratinocytes which are autologous with respect to an intended recipient. In general, this embodiment relies on harvesting the patient's own epithelium-forming cells, expanding them ex vivo, and seeding the expanded cells on cell scaffolds for delivery according to the methods of the invention. By increasing the number of the patient's own epidermal stem cells and incorporating them directly into the inventive composition, a normal and fully-functional multilayer skin can be restored using the body's own natural repair mechanism.

The cellular scaffold of the invention may be manufactured using any precursor keratinocyte cell population that is capable of being cultured in the layered cellular scaffold of the invention. In some embodiments, the precursor keratinocytes are basal precursor cells that express at least one of cell markers CK-14 and CK-19.

1a. Tissue Preparation

In one embodiment, the inventive composition is seeded with precursor keratinocytes. As noted above, precursor keratinocytes can be isolated from a wide range of epithelial tissues including the basal epidermis, the hair bulge, the cornea limbus and neonatal foreskin. Tissue sources for precursor keratinocytes include adult and prenatal tissues from human and non-human sources.

Isolating precursor keratinocytes from the basal layer of the epidermis can be done using the split dermis technique as disclosed in U.S. Pat. Nos. 5,834,312 and 7,037,721, the disclosures of which are incorporated herein by reference. In general, the split dermis technique begins by removing epidermal tissue using any suitable surgical technique, and subjecting the tissue to enzymatic digestion. Enzymes suitable for the digestion of the epithelial tissue include trypsin, chymotrypsin, collagenase, elastase, hyaluronidase, Dnase, pronase, and/or dispase. Following digestion, the dermal and epidermal layers are separated when the cornified side of the epidermis is placed on a clean sterile polystyrene surface whereupon the epidermis spontaneously detaches, and the dermis is removed with sterile forceps. Following separation of dermis from epidermis, the epidermis is dissociated into essentially single cells to form a suspension of epidermal cells in a liquid medium. Disassociation of the cells may be accomplished mechanically provided that shearing forces are avoided. Mechanical disassociation may be accomplished by stirring at low speeds, vortexing, pipetting, and other forms of mixing. Disassociation of the epidermis can also be accomplished with chelating agents that weaken the connections between neighboring epidermal cells.

Mechanical separation may be used to obtain a cell preparation with or without enzymatic digestion. Mechanical devices for this purpose include grinders, blenders, sieves, homogenizers, pressure cells, or insonators (Freshney, Culture of Animal Cells. A Manual of Basic Technique, 2d Ed., A. R. Liss, Inc., New York, 1987, Ch. 9, pp. 107-26; incorporated herein by reference).

Although isolation from the basal epidermis is specifically disclosed, one skilled in the art will appreciate that the precursor keratinocytes of the invention may be derived from any epithelial tissue including neonatal foreskin. Neonatal foreskin is a particularly good source of precursor keratinocytes because it is composed of up to 10% precursor keratinocytes (Toma, J. G. "Isolation and characterization of multipotent skin-derived precursors from human skin" 2005 June-July; 23(6):727-37).

1b. Precursor Keratinocyte Isolation

The precursor keratinocytes of the inventive composition may be isolated through a variety of techniques known in the art. Without limitation, these techniques include calcium stripping, fluorescence-activated cell-sorting (FACS) and collagen selection.

i. Calcium Stripping

The epithelial stem cells of the inventive composition are preferably isolated by calcium stripping. Calcium stripping is a process by which terminally differentiated keratinocytes are separated from the precursor keratinocytes of the basal epithelium. The procedure generally involves the culture of a mixed population of keratinocytes in a calcium-free medium having less than $10^{-6}$ M calcium cations.

Calcium stripping as a means for isolating precursor keratinocytes is well documented in the art as demonstrated by the detailed procedures set out in U.S. Pat. Nos. 5,686,302, 5,834, 312, 6,087,168, Hakkinen, L. "An improved method for culture of epidermal keratinocytes from newborn mouse skin" Methods Cell Sci. (2001) 23 (4): 189-196, Price, F. M. "Approaches to enhance proliferation of human epidermal keratinocytes in mass culture" J. Natl. Cancer Inst. (1983) 70(5):853-861; Babcock, M. S. "Clonal growth and serial propagation of rat esophageal epithelial cells" In Vitro (1983) 19(5):403-415, and Jensen, P. K. "Low Ca++ stripping of differentiation cell layers in human epidermal cultures: an in vitro model of epidermal regeneration" Exp. Cell Res. (1988) 175(1):63-73. The disclosures of these documents are incorporated herein by reference.

ii. FACS

FACS is a procedure wherein ligand/signal conjugates are used to separate cells based on their cell-surface receptor profile. This method lends itself to the separation of precursor keratinocytes from other cells of the epidermis due to the differential expression of surface β ntegrin. β integrins are heterodimeric glycoprotein adhesion receptors that secure precursor keratinocytes to the matrix proteins of the basement membrane. Because precursor keratinocytes express high levels of β integrin relative to other cells of the epidermis, FACS can be used to separate precursor keratinocytes from the remaining epidermal cells. Procedures for isolating precursor keratinocytes using FACS are detailed in U.S. Patent Application US20060073117A1 and U.S. Pat. No. 6,485,971 B1, the disclosures of which are incorporated herein by reference.

In some embodiments of the invention, FACS is used to isolate CK19 positive precursor keratinocyte cells.

iii. Collagen Selection

Isolating precursor keratinocytes by collagen selection also relies on the cells' relatively high level of β integrin expression. β integrins have a particular affinity for type IV collagen molecules. Thus, substrates coated with type IV collagen may be used to select precursor keratinocytes from a mixed population of cells. Procedures for isolating precursor keratinocytes using collagen selection are documented in the art (see e.g. "Separation of Human Epidermal Stem (Cells from Transit Amplifying Cells on the Basis of Differences in Integrin Function and Expression" Cell 73:713-723 (1993) (incorporated herein by reference)).

iv. Selective Media Expansion

Precursor keratinocytes for manufacturing the cellular scaffold may be isolated through selective media. One skilled in the art will appreciate that any media formulation that selectively expands precursor keratinocytes from a mixed population of cells may be used. Example 2 below details one method by which precursor keratinocytes are preferentially expanded (i.e. isolated) using PCT medium (Progenitor Cell Targeting Medium (Cat#CnT-07, Chemicon).

2. Mesenchymal Cells

2a. Mesenchymal Cell Characteristics

Like their ectodermal counterpart, the mesenchymal cells of the invention may differ in their level of potency and degree of specialization. Thus, mesenchymal cell potency can range from multipotent mesenchymal stem cells that can form all cells of the mesoderm lineage, down to fully differentiated terminal cells including, but not limited to, fibroblasts, osteocytes, myocytes and chondrocytes.

Multipotent mesenchymal cells for making the cellular scaffold may be derived from a variety of sources. In one aspect of the invention, the multipotent mesenchymal cells are derived from embryonic mesoderm tissue. In another aspect of the invention, multipotent mesenchymal cells are derived from adult tissues, including, but not limited to bone marrow, peripheral blood and adipose tissue. It is also within the scope of the invention to isolate multipotent mesenchymal stem cells from tissues such as umbilical cord blood and placenta.

One aspect of the invention relates to seeding the scaffold with lineage-committed precursor mesenchymal cells which are programmed to differentiate into specific types of mesenchymal or connective tissues including, but not limited to, dermis, muscle, bone, cartilage, fat, blood, marrow stroma and tendon. The mesenchymal cells of the invention may be derived from, for example, a fibroblast precursor. Such precursor cells are lineage-committed cells in the sense that they are incapable of differentiating into cells of a different lineage, yet remain capable of dividing to form new fibroblast precursors. The mesenchymal cells of the invention further include terminally specialized cells which have differentiated to perform a specific function. Examples of such specialized mesenchymal cells include fibroblasts, striated- and smooth-muscle cells, heart-muscle cells, and blood platelets.

The mesenchymal cells of the invention may be derived from a variety of tissues. For example, mesenchymal cells can be isolated from embryonic tissues, fetal tissues, neonatal tissues, adult tissues, fetal cord blood, placenta and combinations thereof. The specific tissues that provide a sufficient source of adult mesenchymal cells include, but are not limited to, bone marrow, blood, muscle, skin and adipose tissue.

Mesenchymal cells for seeding the cell scaffold may be derived from human and non-human sources. Thus, when the cellular scaffold is used in tissue engineering, mesenchymal cells for seeding the scaffold may be syngeneic, allogeneic or xenogeneic with respect to the recipient of the cellular scaffold.

One or more layers of the cellular scaffold may be seeded with an inoculum of fibroblasts. The cells in the inoculum may be activate fibroblasts (i.e. viable), inactivated fibroblasts (e.g. irradiated fibroblasts), or a combination thereof. Inactivated fibroblasts may be used to control the proportion of cells in the cellular scaffold. For example, when the cellular scaffold is arranged as a skin equivalent, it may be desirable to control the proportion of fibroblasts relative to precursor keratinocytes. Using an inoculum of irradiation-inactivated fibroblasts prevents the fibroblasts from overpopulating the scaffold and displacing precursor keratinocytes which tend to be less prolific. Inactivated fibroblasts can also be used to make cell scaffolds for treating epithelial wounds in which the derma is left intact.

2b. Mesenchymal Cell Isolation

One skilled in the art will appreciate that mesenchymal stem cells for practicing the invention may be isolated using any suitable technique that produces viable cells capable performing a desired function. The isolation and culture of mesenchymal cells is a highly developed art that has been in practice for many years (see e.g. Werb et al. (1974) J. Biochem. 137, 373-385). Thus, instructions for isolating mesenchymal stem cells are readily available. For example, the following references, which are incorporated by reference, disclose suitable methods for isolating mesenchymal stem cells: U.S. Pat. Nos. 5,486,359; 6,039,760; 6,471,958; 5,197,985; 5,226,914; WO92/22584; U.S. Pat. Nos. 5,827,735; 5,811,094; 5,736,396; 5,837,539; 5,837,670; 5,827,740; Jaiswal, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 41644173; and Makino, S., et al., J. Clin. Invest. (1999) 103(5): 697-705.

In some embodiments of the invention, mesenchymal cells are isolated using cell surface markers. Epitopes on the surface of human mesenchymal stem cells are reactive with certain monoclonal antibodies known as SH2, SH3 and SH4. These antibodies can be used as reagents to screen and capture a mesenchymal stem cell population from a heterogeneous cell population such as that found in the bone marrow (see e.g. U.S. Pat. No. 5,486,359, the disclosure of which is incorporated by reference).

Although in a preferred embodiment the mesenchymal stem cells are expanded before being seeded on the cellular scaffold, it is also possible to seed the scaffold with mesenchymal stem cells without expanding them. For example, mesenchymal stem cells may be derived from bone marrow, separated from blood cells, and seeded onto the cell scaffold of the invention without an intervening expansion step. Thus, for example, allogeneic bone marrow may be enriched in allogeneic human mesenchymal stem cells by removal of blood cells, and seeded onto the scaffold.

Fibroblasts for seeding the scaffold may be derived from an established cell line, or a tissue explant. Methods for culturing fibroblasts for use with the invention are readily available in the art (see e.g. Brun et al. J Mater Sci Mater Med. 1999 October-November; 10(10/11):683-8; Zacchi et al. J Biomed Mater Res. 1998 May; 40(2):187-94; Margulis et al. Methods Mol. Biol. 2005; 289:61-70; and Chen et al. Biomaterials. 2005 May; 26(15):2559-66. chen et al).

3. Cell Scaffolds

One aspect of the invention relates to the composition of the cell scaffold. In general, cell scaffold materials for use with the invention may be derived from any source that provides a biocompatible substrate for cell growth and/or the implantation of cells in an animal. Such materials may be biodegradable or non-biodegradable, as well as combinations thereof. When a biodegradable scaffold material(s) is used for implantation, the scaffold should remain within the body of an animal long enough for regenerative cells seeded on the scaffold to divide, differentiate, and begin to replace or supplement the tissues the cells are designed to treat. The scaffold must retain its structural integrity until an adequate number of cells have reproduced within the scaffold to regenerate the lost or removed tissue. If the scaffold is degraded more quickly than this, it will be liquified and rendered useless before the wound has healed. On the other hand, if the lattice is biodegraded too slowly, it tends to promote the formation of a dense fibrotic tissue surrounding the lattice. This impedes the healing of the wound and promotes scarring.

The cell scaffolds of the invention may be derived from natural materials, synthetic materials, and combinations thereof. Natural materials for manufacturing the structural component of the invention include, but are not limited to, polysaccharides, peptides, proteins and combinations thereof. The skilled artisan will appreciate that the substrate of the invention is not limited to any particular material or formulation.

3a. Natural Scaffold Materials i. Proteinaceous Scaffolds

The scaffold of the present invention may be derived from collagen. Collagen is the most abundant animal protein and the major protein of skin and connective tissue. In terms of structure, collagens are a family of fibrous proteins that are secreted by connective tissue cells, as well as by a variety of other cell types. See generally, Alberts, B., et al., Molecular Biology of the Cell, 3rd Ed., Garland Publishing, New York (1994) pp. 978-984. The characteristic feature of a typical collagen molecule is its long, stiff, triple-stranded helical structure, in which three collagen polypeptide chains, called .alpha. chains, are wound around one another in a rope-like superhelix.

Collagen is a suitable scaffold material due to its abundance and high degree of homology between human and non-human forms of collagen. Accordingly, animal collagen provides a vast reservoir of relatively non-immunogenic scaffold material. Animal collagen for use with the inventive composition may be derived from humans, cows, pigs, sheep, goats, rabbits, mice, rats, horses or any other animal that serves as a reservoir of collagen that is biocompatible and supports the culture and/or implantation of the cells disclosed herein. Preferably, the inventive composition comprises porcine collagen due to its low antigenicity. The present invention is not limited to animal collagen as one skilled in the art will appreciate that any form of biocompatible collagen may be used. For example, the invention also encompasses collagen scaffolds derived from solid-phase protein synthesis and recombinant DNA technology. The scaffold of the invention may be derived with any form of biocompatible collagen, including collagen types I, II, III, V and XI (used singularly or in combination). Type I collagen is well suited for use with the invention due to its availability, ease of purification, and proven biocompatible properties.

There are a number of methods known in the art for processing animal collagen for use as a cell scaffold. U.S. Pat. No. 2,610,625, the disclosure of which is incorporated by reference, teaches the extraction of collagen from animal tendon using acetic acid.

Another method for extracting collagen is disclosed in Japanese Unexamined Patent Publication No 43734/1993 (incorporated herein by reference) which teaches the isolation of collagen using a lipophilic organic solvent. Collagens can also be prepared by conventional methods such as those disclosed in the following publications, the disclosures of which are incorporated by reference: "Methods in Enzymology," vol. 82, pp. 33-64, 1982; "The Preparation of Highly Purified Insoluble Collagen, Oneson, I, et al. J. Am. Leather Chemists Asso., Vol. LXV, page 440-450, 1970;" and U.S. Pat. Nos. 3,934,852; 3,121,049; 3,131,130; 3,314,861; 3,530,037; 3,949,073; 4,140,537; 4,233,360 4,488,911; and 5,428,022.

Collagen cell scaffolds suitable for use with the invention are commercially available. Without limitation, the cellular scaffold of the invention may be used manufactured using Surgifoam®, Surgicel® and Instat® (each produced by Johnson & Johnson), Apligraf® (Organogenesis Inc.) Alloderm® (Lifecell Corp.), Integra® (Interga LifeSciences Co.) and Terudermis® (Terumo Co.).

Processes for purifying collagen may be altered to obtain a collagen scaffold having desired characteristics. For example, the extraction procedure may be modified to achieve a collagen scaffold having a desired crosslinking density. Crosslinking of collagen fibrils may be introduced in order to increase the scaffold's resistance to hydrolytic and enzymatic degradation when the scaffold is placed in the body of an animal. Accordingly, one skilled in the art will appreciate that collagen extraction methods may be designed to increase crosslinking density by adjusting the type and concentration of crosslinking agent(s), adjusting pH, time and the temperature of incubation in the liquid phase.

The scaffold of the invention may be derived from modified and/or unmodified forms of collagen. For example, functional modifications may be introduced which decrease the rate at which the collagen scaffold is absorbed by the body. This may be accomplished by a number of methods known in the art including increasing the content of glycosaminoglycan (GAG) that is crosslinked with collagen, decreasing the porosity of the collagen scaffold, and as noted above, increasing the scaffold's overall crosslinking density.

Crosslinking density may be modified by a number of means known in the art including heat-dehydration crosslinking and chemical crosslinking. Chemical crosslinking agents include, but are not limited to, glutaraldehyde, formaldehyde and like aldehydes, hexamethylene diisocyanate, tolylene diisocyanate, and like diisocyanates, ethyleneglycol diglycidylether, and like epoxides, and carbodiimide hydrochlorides such as glutaraldehyde. Generally, chemical crosslinking can be carried out using any reagent which can link the side chains of different collagen molecules such as the amino group of lysine or hydroxylysine, the hydroxyl group of serine, threonine or tyrosine, the guanidino group of arginine, the carboxyl group of glutamic or aspartic acid, and the imidazo group of histidine. Chemical reagents for crosslinking these molecules include, but are not limited to, chromium sulfate, formaldehyde, glutaraldehyde, carbodiimide, adipyl chloride and hexamethylene diisocyanate (see e.g. U.S. Pat. No. 6,039,760, incorporated herein by reference). Crosslinking collagen using covalent modification by a mucopolysaccharide according to U.S. Pat. No. 4,280,954, (the disclosure of which is incorporated herein by reference) is also within the scope of the present invention.

One skilled in the art will appreciate that any method for producing a functional collagen modification may be used. For example, crosslinking may be increased by dehydrothermal crosslinking (e.g. producing a collage scaffold in the presence of heat and a vacuum) and dye mediated photooxidation. The invention further contemplates crosslinking fibrillar collagen using D(-)ribose as disclosed in U.S. Pat. Nos. 4,971,954 and 5,955,438, the disclosures of which are incorporated by reference.

Another possible scaffold material for practicing the invention is blood plasma protein. Blood plasma protein can be solidified into a cell-compatible matrix by exposure to transexamic acid (plasminogen inhibitor). The cell scaffold of the invention can also be manufactured from plasma protein by freeze-drying (see e.g. U.S. Pat. No. 7,009,039).

The cellular scaffold of the invention may be derived from fibrin. Fibrin scaffolds may be derived from fibrin alone, or they may comprise a hybrid of fibrin and one or more other biocompatible materials such as collagen. For example, U.S. Pat. No. 4,453,939 discloses a scaffold comprising collagen, a fibrinogen component, a thrombin component, and optionally a fibronectin component. U.S. Pat. No. 4,970,298 discloses another example of a fibronectin-derived scaffold which comprises a scaffold comprising collagen, hyaluronic acid, and fibronectin. Although scaffolds comprising fibrin and another natural material are disclosed here, the invention also contemplates hybrid scaffolds comprising fibrin in combination with one or more synthetic biocompatible materials. Thus, biocompatible materials for use with a fibrin scaffold include natural and synthetic materials, as well as combinations thereof.

Another aspect of the invention relates to treating tubular epithelial defects using a scaffold derived from elastin. Scaffolds according to this embodiment may be derived from elastin alone, or elastin in combination with one or more other biocompatible materials. U.S. Pat. No. 7,029,689 (incorporated by reference) discloses one such embodiment which comprises a scaffold derived from elastin and collagen. Other non-limiting examples of elastin-derived scaffolds for manufacturing cellular scaffolds are disclosed in the following publications, the disclosures of which are incorporated by reference: Hafemann, B. "Use of a collagen/elastin-membrane for the tissue engineering of dermis" *Burns* (1999) 25 (5): 373-384; de Vries, H. J. "Stromal cells from subcutaneous adipose tissue seeded in a native collagen/elastin dermal substitute reduce wound contraction in full thickness skin defects" *Lab Invest.* (1995) 73 (4): 532-40; Lamme, E. N. "Extracellular matrix characterization during healing of full-thickness wounds treated with a collagen/elastin dermal substitute shows improved skin regeneration in pigs" *J. Histochem. Cytochem.* (1996) 44 (11): 1311-22. These references further disclose methods for purifying elastin, as well as methods for manufacturing elastin cell scaffolds. Methods for purifying elastin include, but are not limited to, neutral extraction, alkaline extraction, and non-degradative processes. One skilled in the art will appreciate that any source of biocompatible elastin may be used to manufacture the cell scaffold of the invention and that the ratios between elastin and other biocompatible substances to be used with the scaffold may be varied according to the use for which the scaffold is to be applied.

As with the other cell scaffold materials, elastin may be modified to achieve a desired characteristic. One non-limiting example of such a modification comprises crosslinking elastin by the introduction of crosslinking sequences (e.g. RGD amino acid binding sequences). These crosslinking sequences may be introduced as a means for enhancing cell-matrix binding.

In some embodiments, the cellular scaffold of the invention may be made using scaffolds derived from one or more types of peptide. These peptides are self-assembling and aggregate to form a three-dimensional matrix suitable for the culture and engraftment of the cells disclosed herein. They are also biodegradable, biocompatible, and support the growth and/or engrafment of regenerative cells. Peptides useful as a cell scaffold are preferably biodegradable at a rate that permits the scaffold to be absorbed by the body, yet remain long enough for angiogenesis to take place such that the cells within the scaffold are sufficiently supported by bodily fluids. Peptides for use with the invention form a scaffold by self assembling into a matrix having sufficient porosity to permit the growth of cells seeded onto the scaffold, as well as the ingrowth of cells from the body when the scaffold is implanted in an animal.

The cell scaffold of the invention may be manufactured using any peptide that is biocompatible and capable of supporting the culture and engraftment of the cells disclosed herein. Such peptides, when implanted in an animal, allow the invasion of cells from the wound edge as well as the development of the vasculature necessary to incorporate the scaffold as a portion of the body. Peptide scaffolds according to the invention are biodegradable and are preferably absorbed by the body at a rate that permits the scaffold to correct the tissue defect for which the scaffold is applied. Non-limiting examples of peptide cell scaffolds suitable for use with the invention include, but are not limited to, U.S. Pat. Nos. 6,800, 481 and 5,955,578.

ii. Polysaccharide Scaffolds

Cell scaffolds for making the composition of the invention may be derived from one or more polysaccharides. Such scaffolds may be composed of one or more polysaccharides entirely, as well as hybrids comprising a polysaccharide in combination with one or more other biocompatible materials. The polysaccharide scaffolds of the invention may also comprise a singular (i.e. homogenous) population of polysaccharide molecules, or a combination of one or more different polysaccharides. It is also contemplated that the scaffold may optionally comprise polysaccharides that have been modified such as by the addition of chemical groups. Polysaccharides for manufacturing the inventive scaffold include, without limitation, chitin, hyaluronic acid, and glycosaminoglycan derivatives.

Cell scaffolds of the invention may be derived from chitin. Chitin, as used herein, refers to a polysaccharide composition prepared from the shells of arthropods, particularly crustacean or insects. It is biocompatible and naturally resorbed by the body, and has been previously used for sustained drug release, bone induction and hemostasis (see e.g. Chandy and Sharma, *Biomat. Art. Cells & Immob. Biotech.* (1991) 19:745-760, Hou et al., *Chem. Pharm. Bull.* (1985) 33 (9): 3986-3992, and Klokkevold, P. *J. Oral Maxillofac. Sur.* (1992) 50:41-45, the disclosures of which are incorporated herein by reference). Cell scaffolds may be manufactured with unmodified and/or modified forms chitin.

"Chitosan" is a modified form of chitin and provides one example of a suitable polysaccharide scaffold. "Chitosan," as used herein, includes any polysaccharide produced by hydrolysis of acetamido groups of N-acetyl glucosan in chitin. Also within the scope of the invention are scaffolds derived from NOC-chitosan, a water soluble chitin derivative formed by carboxymethlyation of biomedical grade chitosan. U.S. Pat. No. 4,619,995, incorporated herein by reference, sets forth the composition and preparation of NOC-chitosan. Chitin and its derivatives can be prepared in powder or solid form from freeze- or air-dried chitin, or from ground chitin as originally produced. Also within the scope of the invention are scaffolds derived from cross-linked chitin derivatives (see e.g. Adekogbe, I. "Fabrication and characterization of DTBP-crosslinked chitosan scaffolds for skin tissue engineering" *Biomaterials* (2005) 26 (35):7241-50, incorporated herein by reference). Other non-limiting examples of chitin scaffolds, and methods for their manufacture, are set forth in U.S. Pat. No. 6,124,273 (disclosing chitin and chitosan hydrogels), U.S. Pat. Nos. 6,699,287 and 6,642,213, the disclosures of which are incorporated by reference.

The cell scaffolds of the invention may also comprise hybrids of chitin and one or more other biocompatible materials. For example, the invention may be practiced with compositions having varying formulations of chitosan and collagen (Norazril, S. A. "Comparison of chitosan scaffold and chitosan-collagen scaffold: a preliminary study" *Med. J. Malaysia* (2004) 59 Suppl B: 186-7; and Ma, L. "Collagen/chitosan porous scaffolds with improved biostability for skin tissue engineering" *Biomaterials* (2003) 24 (26):4833-41 (both incorporated by reference)) or chitosan and hyaluronic acid (Liu, H. A. "A study on a chitosan-gelatin-hyaluronic acid scaffold as artificial skin in vitro and its tissue engineering applications" *J. Biomater. Sci. Polym. Ed.* (2004) 15(1): 25-40; and Mao, J. S. "The properties of chitosan-gelatin membranes and scaffolds modified with hyaluronic acid by different methods" *Biomaterials* (2003) 24(9):1621-9 (both incorporated by reference)).

Although specific chitin-derived scaffolds have been called out here, the skilled artisan will appreciate that the disclosed cellular scaffold may be practiced with any chitin derivative that is capable of supporting the growth and/or implantation of the cells disclosed herein.

In some embodiments, the cell scaffolds of the invention are derived from hyaluronic acid. Hyaluronic acid is a natural heteropolysaccharide composed of alternating residues of D-glucuronic acid and N-acetyl-D-glucosamine. It is a linear polymer with a molecular weight of between 50,000 and 13,000,000 depending upon the source from which it is obtained, and the preparation and determination methods employed. Hyaluronic acid is the primary substance of vertebrate connective tissues and one of the main components of synovial joint fluid, the vitreous humor and human umbilical cord tissues. As used herein, "hyaluronic acid" is intended to include the various forms of hyaluronic acid (HA) known in the art. These various forms include HA chemically modified (such as by cross-linking) to vary its resorbtion capacity and/or its ability to be degraded.

HA scaffolds for use with the invention are available in the art. One example of such a scaffold is disclosed by Ji et al. (Ji, Y. "Electrospun three-dimensional hyaluronic acid nanofibrous scaffolds" *Biomaterials* (2006) 27(20): 3782-92 (incorporated by reference)). According to this embodiment, the scaffold comprises a three-dimensional nanaofibrous matrix based on a thiolated HA derivative. This scaffold may be crosslinked by adding poly(ethylene glycol)-diacrylate to increase resistance to resorbtion when implanted in an animal body.

As with the other scaffold materials discussed above, HA may be the only component of the scaffold, or it may be combined with one or more other biocompatible materials to create a hybrid scaffold. That is, the scaffold may be a homogenous composition of HA, or a blend of HA and at least one other biocompatible substance. Without limiting the scope of potential hybrid HA scaffolds, the cellular scaffold disclosed herein may be practiced with a combination of HA and one or more of chitin, collagen and chondroitin-sulfate. Examples of such scaffolds, and their methods of preparation, are available in the art (see e.g. U.S. Pat. No. 6,773,723 (disclosing a hybrid scaffold of HA and collagen); U.S. Pat. No. 5,955,578 (disclosing a scaffold comprising self-assembling peptide and HA); Liu, H. "Construction of Chitosan-Gelatin-Hyaluronic Acid Artificial Skin In Vitro" *J. Biomater. Appl.* (2006) May 9 [Epub ahead of print]; Wang, T. W. "Biomimetic bilayered gelatin-chondroitin 6 sulfate-hyaluronic acid biopolymer as a scaffold for skin equivalent tissue engineering" *Artif. Organs.* (2006) 30(3): 141-9; and Wang, T. W. "Organotypic keratinocyte-fibroblast cocultures on a bilayer gelatin scaffold as a model of skin equivalent" *Biomed. Sci. Instrum.* (2003) 39:523-8) (these and other references cited in the specification are incorporated by reference in their entirety)). It is contemplated that the scaffold of the invention may be derived from HA and any other biocompatible material that supports the culture and/or engraftment of the cells disclosed herein.

Scaffolds for making cellular scaffolds may be derived from modified or unmodified forms of HA. Depending on the particular needs of a treatment or application, HA may be altered to modulate the rate at which the scaffold is absorbed by the body. Modifications that control HA biodedgradation include the esterification of carboxy groups (see e.g. U.S. Pat. Nos. 4,851,521, 4,965,353 and 5,520,916) and crosslinking. Crosslinking of HA may be performed using chemical agents including, but not limited to, glutaraldehyde and water-soluble carbodiimide, such as disclosed in U.S. Pat. No. 6,803,037. The present invention further contemplates any HA modification that produces a scaffold suitable for the manufacturing of the inventive cellular scaffold.

iii. Other Natural Scaffold Materials

Although specific natural scaffold materials are disclosed above, the cellular scaffold of the invention may be made using any variety of natural polymers, alone or in combination, which support the culture and/or implantation of cells. Examples of these polymers include without limitation alginate, cellulose, dextran, pullane, polyhyaluronic acid, polyglycolic acid, poly(3-hydroxyalkanoate), poly(3-hydroxyoctanoate), poly(3-hydroxyfatty acid), albumin, fibronectin, vitronectin, laminin, dextran, dextran sulfate, chondroitin sulfate, dermatan sulfate, keratan sulfate, heparin, heparin sulfate and alginate. Also contemplated within the invention are chemical derivatives of said natural polymers including substitutions and/or additions of chemical groups such as alkyl, alkylene, hydroxylations, oxidations, as well as other modifications familiar to those skilled in the art.

3b. Synthetic Substrate Materials

Cell scaffolds for practicing the invention may be derived from synthetic material(s).

Scaffolds according to these embodiments may be derived from one or more synthetic materials, or they may comprise a mixture of synthetic and natural materials. Synthetic materials for making the scaffold of the present invention are biocompatible and biodegradable (e.g. subject to enzymatic and hydrolytic degradation).

In one aspect of the invention, the cellular scaffold incorporates polylactic acid (PLA). PLA is particularly suited to tissue engineering methods using the cellular scaffold as PLA degrades within the human body to form lactic acid, a naturally occurring chemical which is easily removed from the body. The cellular scaffold of the invention may also incorporate polyglycolic acid (PGA) and/or polycaprolactone (PCL) as scaffold materials. PGA and PCL have similar degradation pathways to PLA, but PGA degrades in the body more quickly than PLA, while PCL has a slower degradation rate than PLA. PGA has been widely used in tissue engineering. PGA scaffolds can be easily manipulated into various three dimensional structures, and offer an excellent means of support and transportation for cells (Christenson L, Mikos A G, Gibbons D F, et al: Biomaterials for tissue engineering: summary. *Tissue Eng.* 3 (1): 71-73; discussion 73-76, 1997). Scaffolds manufactured from polyglycolic acid alone, as well as combinations of PGA and other natural and/or synthetic biocompatible materials, are within the scope of the invention.

The cellular scaffold of the invention contemplates scaffolds made from PGA, PLA and PCL that has been modified. These modifications may include, without limitation, chemical substitutions and the addition of chemical groups by covalent bonding (see e.g. Labhasetwar, V "Arterial uptake of biodegradable nanoparticles: Effect of surface modifications" *J. Pharm. Sci.* (2000) 87(10):1229-1234). (see e.g. Park, A. "Integration of surface modification and 3D fabrication techniques to prepare patterned poly(L-lactide) substrates allowing regionally selective cell adhesion" *J. Biomater. Sci. Polym. Ed.* (1998) 9(2):89-110), In one aspect of the invention, the cellular scaffold incorporates one or more synthetic polymers in its construction. The cellular scaffold may be made from heteropolymers, monopolymers, or combinations thereof. Examples of polymers suitable for manufacturing cell scaffolds include, but are not limited to aliphatic polyesters, copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules and blends thereof. For the purpose of this invention aliphatic polyesters include but are not limited to homopolymers and copolymers of lactide (which includes lactic acid, D-,L- and meso lactide), glycolide (including glycolic acid), .epsilon.-caprolactone, p-dioxanone (1,4-dioxan-2-one), trimethylene carbonate (1,3-dioxan-2-one), alkyl derivatives of trimethylene carbonate, .delta.-valerolactone, .beta.-butyrolactone, .gamma.-butyrolactone, .epsilon.-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in "Journal of Biomaterials Research", Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and .epsilon.-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form HOOC—C.sub.6H.sub.4—O—(CH.sub.2).sub.m—O—C.sub.6H.sub.4—COOH where m is an integer in the range of from 2 to 8 and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference).

The cellular scaffolds of the invention may incorporate aliphatic polyesters which can be homopolymers, copolymers (random, block, segmented, tappered blocks, graft, triblock, etc.) having a linear, branched or star structure. Preferred are linear copolymers. Suitable monomers for making aliphatic homopolymers and copolymers may be selected from the group consisting of, but are not limited to, lactic acid, lactide (including L-, D-, meso and D,L mixtures), glycolic acid, glycolide, .epsilon.-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Elastomeric copolymers also are particularly useful in the present invention. Suitable bioabsorbable biocompatible elastomers include but are not limited to those selected from the group consisting of elastomeric copolymers of .epsilon.-caprolactone and glycolide (preferably having a mole ratio of .epsilon.-caprolactone to glycolide of from about 35:65 to about 65:35, more preferably from 45:55 to 35:65) elastomeric copolymers of .epsilon.-caprolactone and lactide, including L-lactide, D-lactide blends thereof or lactic acid copolymers (preferably having a mole ratio of .epsilon.-caprolactone to lactide of from about 35:65 to about 65:35 and more preferably from 45:55 to 30:70 or from about 95:5 to about 85:15) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of .epsilon.-caprolactone and p-dioxanone (preferably having a mole ratio of .epsilon.-caprolactone to p-dioxanone of from about from 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. Examples of suitable bioabsorbable elastomers are described in U.S. Pat. Nos. 4,045,418; 4,057,537 and 5,468,253 all hereby incorporated by reference. These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25.degree.C. in a 0.1 gram per deciliter (g/dL) solution of polymer in hexafluoroisopropanol (HFIP).

The invention contemplates the use the polymers alone, copolymers, or blends thereof to fabricate cellular scaffolds. Selection of the polymer combinations will depend upon the particular application and include consideration of such factors as desired tensile strength, elasticity, elongation, modulus, toughness, viscosity of the liquid polymer, whether biodegradable or permanent structures are intended, and the like to provide desired characteristics.

Other materials suitable for use as a cellular scaffold include, but are not limited to, polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, polyvinyl alcohols, polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Synthetic polymers can further include those selected from the group consisting of aliphatic polyesters, poly(amino acids), poly(propylene fumarate), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Examples of appropriate aliphatic polyesters include, but are not limited to, homopolymers and copolymers of lactide (which includes lactic acid, D-,L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997). Polyanhydrides include those derived from diacids of the form $HOOC-C_6H_4-O-(CH_2)_m-O-C_6H_4-COOH$, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al., Hardwood Academic Press, pp. 99-118 (1997).

4. Substrate Consistency

Another aspect of the invention concerns the consistency of the different layers of the cellular scaffold. The individual layers of the scaffold may have the same or different consistencies. One skilled in the art will appreciate that the layers of the cell scaffold may take on any consistency that allows the scaffold to be used for cell culture, tissue regeneration and/or cell-based assays. It is also desirable that the consistency be such that it supports the growth and division of ectodermal and mesenchymal cells, as well as the invasion of endogenous cells when the cellular scaffold is implanted in an animal.

Scaffolds that satisfy these requirements and are otherwise suitable for practicing the invention may resemble a sponge, (i.e. foam) a gel, a fabric, or combinations thereof. Collagen spongiform scaffolds, or "collagen sponges" have a suitable consistency for manufacturing the cellular scaffold of the invention. Collagen sponges are highly absorbent and demonstrate low antigenicity. Collagen sponges can also achieve a porosity that is ideal for cell seeding and in situ cell invasion when the scaffold is implanted in the body. The porosity of collagen sponges for practicing the invention may vary depending on the particular application for which the cellular scaffold is used. One skilled in the art will appreciate the porosities that a given application requires. Examples of collagen sponges with varying degrees of porosity, and their methods of manufacture, are provided in the following publications, the disclosures of which are incorporated herein by reference: U.S. Patent Nos. 2,610,625, 3,157,524, 3,368,911, 6,500,464, 6,039,760 and 6,835,336.

Collagen sponges for practicing the invention are commercially available. One example of such a scaffold is Gelfoam™. Gelfoam™ is an absorbable gelatin sponge that has been used in surgical procedures and as a topical hemostatic agent since the mid 1940's. Gelfoam, manufactured by Upjohn, is a water insoluble, off-white, non-elastic, porous, pliable product prepared from purified porcine skin collagen (see e.g. Sorour et al., (1975) J. Neurosurg. 43:742-749).

Another commercial spongiform scaffold for practicing the invention is Spongostan™ (produced by the Ethicon division of Johnson & Johnson). Spongostan™ is a porcine-derived resorbable collagen matrix. It is a medical device intended for application to bleeding surfaces as a hemostatic. Like the other spongiform scaffolds, Spongostan's physical properties make it suitable for treating tubular epithelial defects. That is, Spongostan™ is porous, pliable and strong enough to resist breaking when used according to the methods disclosed herein. Other commercial collagen sponges for use with the invention include Helistat™ (produced by Marion Merrell Dow of Kansas City, Mo.) and those manufactured by Becton Dickinson.

Spongiform scaffolds for practicing the invention may also be derived from one or more non-collagenous materials. U.S. Pat. No. 6,793,675, for example, discloses three-dimensional, porous, biodegradable sponges made from polyanionic polysaccharide polymers including gellan, gellan gum, xanthan chitosan, agar, carrageenan, and polycationic polysaccharide polymers such as chitosan. Other materials suitable for making sponge-like cell scaffolds include chitosan (U.S. Pat. No. 6,693,180), hyaluronic acid (U.S. Pat. Nos. 6,548,081 6,096,727 and 6,537,979), cellulose with collagen (Leighton et al., (1968) Cancer Res. 28:286-296), and cellulose alone (Leighton et al., (1951) J. Natl Cancer Inst. 12:545-561).

One or more of the individual layers of the cellular scaffold may assume the consistency of a gel, or, hydrogel. Hydrogels are colloids in which a polymer is combined with water to produce a viscous, jellylike product. Like spongiform scaffolds, hydrogels have long been used in tissue engineering. Hydrogels for use with the invention may be derived from any non-toxic, resorbable biocompatible material that supports the culture and/or implantation of cells.

Hydrogels suitable for making the layered cellular scaffold may be derived from a variety of materials. In one aspect of the invention, the cellular scaffold incorporates collagen hydrogels. Examples of suitable collagen hydrogels, and their manufacture, are disclosed in the following references: U.S. Pat. No. 6,335,007 (teaching a collagen gel that is crosslinked polyanion and carbodiimide); U.S. Pat. No. 4,485,096; Douglas et al., (1980) In Vitro 16:306-312; Yang et al., (1979) Proc. Natl. Acad. Sci. 76:3401; Yang et al. (1980) Proc. Natl. Acad. Sci. 77:2088-2092; and Yang et al. (1981) Cancer Res. 41:1021-1027. In another aspect of the invention, the cellular scaffold comprises one or more layers which are derived from chitin. Chitin gels suitable for use with the invention include those disclosed in the following references, the disclosures of which are incorporated herein by reference: U.S. Pat. Nos. 6,025,479; 6,124,273; 6,335,007; Noble et al. (1999) Int. J. Pharm. 192(2):173-82; Koyano et al. (1998) J. Biomed. Mater. Res. 5; 39(3):486-90; Zhu et al. (2005) J. Biomater. Sci. Polym. Ed. 6(3):301-16; Freier et al. (2005) Biomaterials 26(22):4624-32; Liu et al. (2005) J Biomater Appl. 19(4):303-22; Huang et al. (2005) Biomaterials 26(36):7616-27.

Other hydrogel scaffolds for practicing the invention include, but are not limited to, hydrogels derived from polymers (see e.g. U.S. Pat. No. 5,716,413) including polylactide and polyglycolide (see e.g. U.S. Pat. Nos. 5,573,934 and 5,626,863) and hyaluronic acid (see e.g. U.S. Pat. No. 6,548,081).

Hydrogels derived from self-assembling peptides are also within the scope of the invention such as, for example, disclosed in WO2006036826 A2 and WO2006014570 A2, the disclosures of which are incorporated by reference. One commercial peptide hydrogel for making the layered cellular scaffold is PuraMatrix manufactured by Becton Dickinson.

In other embodiments of the invention, one or more of the cell scaffolds are derived from a polymeric foam having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. Foam scaffolds for practicing the invention should be pliable enough to be shaped and manipulated according the methods disclosed herein.

Foam scaffolds for practicing the invention may be derived from a variety of materials. For example, U.S. Pat. Nos. 6,365,149 and 6,333,029 (incorporated herein by reference) disclose foam scaffolds derived from a wide range of polymeric materials, wherein the scaffolds are manufactured according to a process that produces a porosity gradient across the scaffold. These scaffolds can be designed to mimic tissue transition or interface zones (e.g. an epithelial tissue interface). Foam scaffolds for practicing the invention may also comprise modified and/or unmodified forms of polyhydroxy acid and copolymers thereof. Such polymers may include, without limitation, poly-L-lactide, poly-DL-lactide, polyglycolide, and polydioxanone. Such scaffolds, and their methods of preparation, are disclosed in the following references, the disclosures of which are incorporated by reference: U.S. patent application No. 20040078090 A1 (disclosing a copolymer foam of 35:65 $\epsilon$-caprolactone and glycolide); U.S. Pat. No. 6,712,850 (disclosing aliphatic polyester copolymer foams comprising polymerized glycolide (including glycolic acid) and .epsilon.-caprolactone); European Patent Application No. 274,898; Hasirci et al. (2001) Tissue Eng. 7(4):385-94 and Mikos et al. (1994) Biomaterials 15(1):55-8 (each disclosing a poly(lactic-co-glycolic) acid biodegradable foam); Danielsson et al. (2006) Biomaterials 27(8):1410-5 (disclosing a polyesterurethane foam scaffold); and Day et al. (2004) J. Mater. Sci. Mater. Med. 15(6):729-34 (disclosing polylactide-co-glycolide (PLGA) foams of tubular shape and their use as soft-tissue engineering scaffolds in vitro and in vivo).

Foams for treating tubular epithelial defects may also be obtained commercially, Avitene™ (produced by MedChem of Woburn, Mass.), for example, is a nonwoven web and fibrous foam that is available in various sizes. DegraPol provides another example of a commercially available foam scaffold which is derived from polyesterurethane (see e.g. Saad et al. (2000) Artif Organs 24(12):939-45). Although specific foam scaffolds have been called out here, the skilled artisan will appreciate that derivatives of these foam materials, as well as their functional equivalents, may be used to practice the invention.

In some embodiments of the invention, the cellular scaffold incorporates a fabric-like scaffold. Fabric-like scaffolds suitable for practicing the invention are manufactured from one or more biocompatible materials that are arranged in a mesh. The mesh may be a woven and/or unwoven framework of biocompatible fibers. Fabric-like scaffolds for practicing the invention may be derived from one or more polysaccharides such as chitin. Chitin fabrics have been used in a variety of tissue engineering applications. U.S. Pat. No. 6,699,287, for example, discloses the preparation and use of a chitosan fabric in wound healing applications. Other polysaccharide materials suitable for practicing the invention include hyaluronic acid. One example of a hyaluronic acid fabric-like scaffold is disclosed in U.S. Pat. No. 5,520,916. This scaffold comprises a non-woven fabric material derived from esters of hyaluronic acid without, and in combination with, esters of alginic acid or other polymers. Fabric-like scaffolds may also be derived from one or more proteins. For example, U.S. Pat. No. 4,089,333 discloses a scaffold spun from regenerated collagen. Other examples of suitable collagen fabrics are available in the following references: Adler et al. Surg Forum. 1962; 13:29-31 (disclosing a collagen mesh for wound repair and hernia reinforcement); Chvapil et al. (1963) J. Surg. Res. 168:358-68 (disclosing the principles and construction of a collagen vascular graft); Jonas et al. (1973) Urol. Int. 1973; 28(3):290-3 (disclosing a collagen graft for partial replacement of the ureter); Chen et al. (2005) Biomaterials. 26(15): 2559-66 (disclosing the culture of skin fibroblasts on a hybrid mesh of poly-lactide, glycolide and collagen); and U.S. Pat. No. 6,916,655 (disclosing the culture and implantation of regenerative cells using a collagen fabric).

The methods of the invention may also be practiced using commercially available fabrics. An example of such a fabric includes, but is not limited to, Dermagraft™ (a polyglactin mesh scaffold by Smith and Nephew). Also within the scope of the invention are fabrics derived from synthetic polymers such as, for example, the fabric disclosed in U.S. Pat. No. 5,770,193 and Slivka et al. (1991) J. Invest. Dermatol. 96: 544A, (disclosing culturing fibroblasts and keratinocytes on a nylon mesh).

It is also contemplated that the invention may use a fabric that is coated with a biocompatible material. One example of this type of scaffold is a chitosan/collagen-coated fabric such as disclosed in Risbud et al. (2003) J Biomater Sci Polym Ed. 14(7):719-31, the disclosure of which is incorporated herein by reference.

In some embodiments of the invention, one or more of the layers of the cellular scaffold is derived from materials having different consistencies. Depending on the type of application it is used for, the scaffold of the invention may take on various compositions. For example, it may be desirable to vary one or more of the scaffold's characteristics such as permeability, stiffness, rate of biodegradation, or porosity (e.g. absorbtion of fluids). One skilled in the art will appreciate the type of scaffold consistency a particular application needs, as well as the combination of materials for meeting that need. In one aspect of the invention, one or more of the cellular scaffold's layers have both porous and gel-like components. One example of such a scaffold is presented in U.S. Pat. No. 7,041,868 which discloses a scaffold having a bioabsorbable, porous first layer adapted for cell attachment and proliferation, and a second layer which comprises an absorbent, gel forming material adapted for serving as a barrier to cell adhesion and penetration.

The invention also contemplates using spongiform scaffolds that are coated with a laminate (e.g. membrane) having a decreased solubility for cells and/or solutes. Examples of such laminated spongiform scaffolds include, but are not limited to, those described in Ma et al. (2001) Biomaterials 22(4):331-6, and U.S. Pat. Nos. 5,976,878, 6,039,760, 6,500,464 and 6,790,454, the disclosures of which are incorporated herein by reference. Integra™ (Integra Life Sciences Co.) is another example of a commercial laminate-coated scaffold suitable for practicing the invention.

In other embodiments of the invention, hybrid scaffolds comprise one or more biocompatible materials that are reinforced with a mesh (e.g. fabric) component. Scaffolds suitable for receiving a reinforcing mesh component include, but are not limited to, sponges, gels and foams. Examples of mesh-reinforced scaffolds for practicing the invention are available in the art as demonstrated by the following publications, the disclosures of which are incorporated herein by reference: U.S. Pat. App. No. 20040078090; Nakanishi et al. (2003) J. Pediatr. Surg. 38(12):1781-4; and European Patent Application No. 274,898. Commercial mesh-reinforced scaffolds that are suitable for practicing the invention include Biobrane™ (Dow Hickam/Bertek Pharmaceuticals) and Transcyte™ (Advanced Tissue Sciences).

Although methods for preparing and seeding scaffolds are disclosed, it is also within the scope of the invention to treat manufacture layered cellular scaffolds using commercial materials that are pre-seeded with cells (see e.g. Jones et al. (2002) Brit. J. of P. Surg. 55:185-193). Examples of pre-seeded scaffolds suitable for use with the invention include, but are not limited to, Dexon™ and Vicryl™ and Transcyte™ (each from Advanced Tissue Sciences, Inc.), Articel™ (Biosurface Technology, Inc.), Apligraft™ (Organogenesis, Inc.) and Alloderm™, (Lifecell).

5. Seeding and Layering the Cell Scaffolds

Seeding the layered cellular scaffold involves introducing one or more desired cell populations to a selected substrate material, and subsequently joining the materials to create a layered cellular scaffold. Alternatively, the individual cell scaffolds may be joined, and the selected population(s) of cells introduced at a selected location. Seeding is distinct from the spontaneous infiltration and migration of cells into the cell scaffold when the scaffold is implanted in the body of an animal.

In one aspect of the invention, the cell scaffolds of the invention are seeded on at least one surface before the respective cell-seeded surfaces are opposed to each other to form a layered arrangement. A cell scaffold is considered "seeded" immediately after it has been inoculated with a viable cell population. The surface of the cell scaffold is also considered seeded if the inoculated cells have divided and infiltrated the scaffold In one aspect of the invention, normal or non-disease state autologous host cells are harvested from an intended recipient and, expanded ex vivo to produce a cell inoculum. It is also within the scope of the invention to use allogeneic cells selected from the same species as a recipient that is intended to receive the cellular scaffold. Alternatively, xenogeneic cells derived from a species that is different than the intended recipient may be used.

Subsequent to isolation, and optionally expansion, the cells to be seeded are placed in a suitable liquid carrier and introduced to the scaffold using a number of seeding techniques known in the art. Examples of seeding techniques for use with the invention include, but are not limited to, spreading, painting, spraying, soaking and pipetting.

The seeding densities of the cellular scaffold may vary and the individual layers of the cell scaffold may have the same or different seeding densities. Seeding densities may vary according to the particular application for which the cellular scaffold is applied. Seeding densities may also vary according to the cell type that is used in manufacturing the cellular scaffold. In some embodiments, the cellular scaffold is manufactured using a scaffold seeded with fibroblasts at a density between about $2\times10^3$ cells/cm$^2$ and $1\times10^6$ cells/cm$^2$, and a scaffold seeded with precursor keratinocytes at a seeding density between about $1\times10^4$ cells/cm and $1\times10^6$ cells/cm$^2$.

Seeding densities of the individual layers of the cell scaffold may vary depending on the use for which the scaffold is intended. One skilled in the art will be able to derive the seeding densities that a specific application requires without investing undue experimentation.

Spreading involves the use of an instrument such as a spatula to spread the inoculum across the spongiform scaffold. Seeding the scaffold by painting is accomplished by dipping a brush into the inoculum, withdrawing it, and wiping the inoculum-laden brush across the spongiform scaffold. This method suffers the disadvantage that substantial numbers of cells may cling to the brush, and not be applied to the lattice. However, it may nevertheless be useful, especially in situations where it is desired to carefully control the pattern or area of lattice over which the inoculum is distributed Seeding the scaffold by spraying generally involves forcing the inoculum through any type of nozzle that transforms liquid into small airborne droplets. This embodiment is subject to two constraints. First, it must not subject the cells in solution to shearing forces or pressures that would damage or kill substantial numbers of cells. Second, it should not require that the cellular suspension be mixed with a propellant fluid that is toxic or detrimental to cells or wound beds. A variety of nozzles that are commonly available satisfy both constraints. Such nozzles may be connected in any conventional way to a reservoir that contains an inoculum of, for example, epithelial stem cells.

Seeding the scaffold by pipetting is accomplished using pipettes, common "eye-droppers," or other similar devices capable of placing small quantities of an inoculum on a scaffold. Pipetting allows the aqueous phase of the cell suspension to permeate the porous scaffold while the cells become enmeshed and retained at the surface of the scaffold.

According to another embodiment of the invention, an inoculum of cells may be seeded by means of a hypodermic syringe equipped with a hollow needle or other conduit. A suspension of cells is administered into the cylinder of the syringe, and the needle is inserted into the scaffold. The plunger of the syringe is depressed to eject a quantity of solution out of the cylinder, through the needle, and into the scaffold.

An important advantage of utilizing an aqueous suspension of cells is that it can be used to greatly expand the area of scaffold on which the cell inoculum is distributed. This provides two distinct advantages. First, if a very limited amount of intact tissue is available for autografting, then suspension methods may be used to dramatically increase the area or volume of a scaffold that may be seeded with the limited number of available cells. Second, if a given area or volume of a scaffold needs to be seeded with cells, then the amount of intact tissue that needs to be harvested from a donor site may be greatly reduced. The optimal seeding densities for specific applications may be determined through routine experimentation by persons skilled in the art.

The number and concentration of cells seeded into or onto a spongiform scaffold can be varied by modifying the concentration of cells in suspension, or by modifying the quantity of suspension that is distributed onto a given area or volume of spongiform scaffold.

One aspect of the invention concerns the dimensions of the cell scaffold that is seeded. The skilled artisan will appreciate that the layered cellular scaffold of the invention can be made using any dimension that permits the culture and/or implantation of cells. In culture, the dimensions of the cell scaffold should be substantially planar and of a thickness that gives seeded cells sufficient access to a nutrient medium. When implanted, the cell scaffold must have sufficient access to body fluids for nutrition and waste removal. The thickness of the cell scaffold may be varied by changes in the scaffold's porosity. Thus, increases in scaffold porosity may permit scaffolds to take on greater thickness as larger pore sizes improve access to external medium and body fluids. In some embodiments, the scaffold does not exceed a thickness of 1.0 mm.

Following seeding, the cell scaffolds are joined to form a layered cellular scaffold. Preferably, the scaffolds are joined after the seeded cells have acclimated to, and infiltrated, the scaffold environment. Cell acclimation and infiltration of the scaffold may take between approximately 8 hours and 3 days, but this time may vary. It is also possible for the individual layers of a cellular scaffold to have different levels of infiltration before joining. In preferred embodiments, the cellular scaffolds are joined before the seeded cells infiltrate the full depth of the cell scaffold.

By way of example only, the cellular scaffold arrangement of the invention may be manufactured by first obtaining a population of ectodermal cells (e.g. precursor keratinocytes) and a population of mesenchymal cells (e.g. fibroblasts). Appropriate, planar, first and second cell scaffolds are selected and prepared for seeding. The scaffolds each have opposing first and second surfaces. After the scaffolds are prepared, the second surface of the first scaffold is seeded with mesenchymal cells (e.g. fibroblasts), and the first surface of the second scaffold is seeded with ectodermal cells (e.g. precursor keratinocytes). The seeded cell scaffolds are then cultured under appropriate conditions to allow the cells to become acclimated to the cell scaffold environment. After an appropriate time, the cell scaffolds are removed from culture and joined such that their seeded surfaces contact one another.

The layered cellular scaffold may also be described as an arrangement having an upper cellular scaffold and a lower cellular scaffold. The upper and lower scaffolds each have a contacting surface that is suitable for seeding with cells. In some embodiments, the cellular scaffold of the invention is manufactured by seeding the contacting surface of the upper scaffold with ectodermal cells (e.g. keratinocytes), and seeding the contacting surface of the lower cellular scaffold with mesenchymal cells (e.g. fibroblasts). After the seeded cells have acclimated to the scaffold environment, the seeded contacting surfaces of the cellular scaffolds are joined to create a layered, sandwich-like structure.

6. Assays

The layered cellular scaffold may serve as a model, or "tissue equivalent," for mimicking the physiology of natural tissues. Different tissues may be mimicked by altering the physical conformation of the cellular scaffold and/or the cells that are seeded on it. For example, the layered cellular scaffold may be used to emulate a living skin, or "skin equivalent," by providing a model having dermal and epidermal layers. This is accomplished, for example, by seeding one scaffold with fibroblasts, seeding another scaffold with precursor keratinocytes, and joining the seeded surfaces of the scaffolds to create a layered arrangement that represents the dermal and epidermal layers of the skin. One skilled in the art will appreciate that the cells and materials used to manufacture the layered cellular scaffold may be varied to achieve a desired tissue model.

Embodiments of the inventive cellular scaffold relate to in vitro, ex vivo and in vivo assays. Accordingly, the cellular scaffold is used for determining the biological activity of pharmaceutical and/or biological agents, including, but not limited to bioactive agents (e.g. cosmetic and pharmaceutical candidates) and electromagnetic/mechanical forces. This utility generally involves contacting the layered cellular scaffold with a test agent, and determining the biological activity that the test agent has on the cells that populate the scaffold. The test agent may be administered to a seeded scaffold in vitro, or it may be administered to the scaffold before and/or after the scaffold is transplanted into a recipient. In this way, the biological effects of the test agent on the seeded cells, or cells that infiltrate the spongiform scaffold from the body of the recipient, may be measured. Biological effects measured via the inventive spongiform scaffold include, but are not limited to cytotoxicity, mutagenicity, proliferation, permeability, apoptosis, cell-to-cell interactions, gene regulation, protein expression, cell differentiation, cell migration, cell cycle regulation and tissue formation. Test agents may be assessed individually or in combination.

The biological activity of a test agent on a tissue equivalent may be measured using a variety of techniques known in the art. Cytoxicity, for example, may be measured using surrogate markers including, but not limited to, neutral red uptake, lactate dehydrogenase release, and malondialdehyde levels (see e.g. Zhu et al. "Cytotoxicity of trichloroethylene and perchloroethylene on normal human epidermal keratinocytes and protective role of vitamin E" *Toxicology* April 1; 209(1): 55-67 Epub 2005 Jan. 7; and U.S. Pat. No. 5,891,161; these disclosures are incorporated herein by reference). Cytoxicity may also be measured by microscopically comparing the numbers of live cells before and after the scaffold is exposed to a test agent.

In some embodiments, the cellular scaffold is used to measure cytotoxicity by detecting the metabolic reduction of a soluble tetrazolium salt to a blue formazan precipitate. The reduction of tetrazolium serves as a marker for cytotoxicity since this reaction is dependent on the presence of viable cells with intact mitochondrial function. This assay is used to quantitate cytotoxicity in a variety of cell types, including cultured human keratinocytes (see e.g. U.S. Pat. No. 5,891, 617 A, incorporated herein by reference). Other methods for measuring cytotoxicity include examination of morphology, the expression or release of certain markers (e.g. receptors and/or enzymes), on DNA synthesis or repair, the release of [$^3$H]-thymidine, the incorporation of BrdU, the exchange of sister chromatids as determined by metaphase spread (see U.S. Pat. No. 7,041,438 B2 and "In vitro Methods in Pharmaceutical Research", Academic Press, 1997; these are incorporated herein by reference), and the differential incorporation of specific dyes by viable and non-viable cells (see e.g. U.S. Pat. No. 6,529,835 B1, incorporated herein by reference).

Due to its ability to support the culture of precursor keratinocytes, the inventive cellular scaffold is particularly suited to evaluating skin toxicity and the efficacy of therapeutics aimed at treating the skin (see Hoh et al. "Multilayered keratinocyte culture used for in vitro toxicology" Mol. Toxicol. 1987-88 Fall; 1(4):537-46, incorporated herein by reference).

In some embodiments the layered cellular scaffold is used in screening methods for identifying agents that promote, inhibit or otherwise modulate the differentiation and/or proliferation of stem cells. There are a number of proliferation and differentiation assays known in the art including those disclosed in U.S. Pat. Nos. 7,037,719, 6,962,698, 6,884,589 and 6,824,973, the disclosures of which are incorporated herein by reference. In general, these assays involve using the inventive cellular scaffold to culture a population of stem cells in the presence of a test agent, and monitoring the proliferative and/or differentiating effects that the test agent imparts on the stem cell population. One skilled in the art will appreciate that there are a number of methods for monitoring these effects including, but not limited to, testing for the presence of lineage-identifying cell surface markers, microscopic analysis of cell morphology, histological examination of extracellular proliferation markers, and cell counts.

The effects of test agents may also be evaluated using histochemical, immunohistochemical, and immunofluorescent methods to establish the presence or absence of specific proteins, glycoproteins, and proteoglycans (Br. J. Dermatol. (2004) 151, (4):753-65). In some embodiments, the tissue equivalent is exposed to a test agent, frozen, embedded in a suitable embedding composition and sectioned for determination of cellular or extracellular enzyme activity and protein functionality. Alternatively, the tissue equivalents may be fixed, embedded in paraffin (or other suitable embedding composition) and sectioned for examination using optical microscopy. Sections of the tissue equivalent (i.e. cellular scaffold) can also be used to assess gene expression by in situ hybridization with nucleotide probes complementary to specific nucleic acid sequences. The thickness of the tissue equivalent may impose a limit on this methodology since the ability to detect labeled cells is impaired by background autofluorescence which increases with thickness. However, single/double photon confocal microscopy can overcome the problem of background autofluorescence. In single/multiple photon confocal microscopy, the tissue is scanned by a laser that only excites the fluorescent marker and background autofluorescence in the plane of the scan, thereby forming optical sections and increasing the effective brightness of the labeled cell compared to the background autofluorescence. Multiple photon evaluation utilizing cells' innate fluorescence (e.g., that due to the NAD/NADH system) can be utilized as well. The latter approach could be applied to living tissue equivalents without having to fluorescently prelable the cells.

7. Inhibiting Precursor Keratinocyte Collagenase Activity

One aspect of the invention concerns inhibiting the collagenase activity of precursor keratinocytes. In their undifferentiated state, basal keratinocytes produce a significant amount of collagenase. This property is believed to allow basal keratinocytes to migrate through the epithelium to populate areas of damaged tissue. This activity however makes it difficult to culture undifferentiated basal keratinocytes on collagen scaffolds since the cells digest the scaffold before it can be put to use.

7a. Inhibiting Collagenase Activity Using Fibroblast/Basal Keratinocyte Co-Culture In one aspect of the invention, the collagenase activity of basal keratinocytes is inhibited by culturing them in the presence of fibroblasts. Fibroblasts, both activated and inactivated (e.g. irradiated), inhibit basal keratinocyte collagenase activity when the basal keratinocytes are cultured under conditions in which they contact, or are at least in close proximity to, fibroblasts.

In some embodiments, the collagenase activity of basal keratinocytes is inhibited using a layered cellular scaffold. This is accomplished by seeding a first surface of a first cell scaffold with basal keratinocytes. The first surface of this scaffold is then juxtaposed (e.g. placed against) to a second scaffold that is seeded on one surface with fibroblasts. The first and second cellular scaffolds are positioned such that the basal keratinocyte-seeded surface of the first cellular scaffold is in substantial contact with the fibroblast-seeded surface of the second cellular scaffold. In some embodiments, the basal keratinocyte-seeded scaffold is cultured in the presence of a substrate (e.g. Petri dish) that is seeded with fibroblasts. This may be accomplished by seeding a surface of the cell scaffold with keratinocytes, and placing the cell-seeded surface of the scaffold in contact with the fibroblast-seeded surface of the Petri dish. Fibroblast seeding densities for inhibiting precursor keratinocyte collagenase activity may range between about $2 \times 10^3$ cells/cm$^2$ and $1 \times 10^6$ cells/cm$^2$.

In the context of the invention, the collagenase activity of basal keratinocytes is inhibited when the activity is lower than that demonstrated by undifferentiated basal keratinocytes which have not been cultured according to the methods of the invention. That is, the collagenase activity of basal keratinocytes is considered to be inhibited when it is lower than that observed for undifferentiated basal keratinocytes which are proliferating under ordinary, non-collagenase-inhibiting in vitro conditions. Collagenase activity according to the invention is evaluated according to the ability of basal keratinocytes to dissolve collagen, such as when the basal keratinocytes are seeded on a collagen scaffold. In a collagenase-inhibited state, basal keratinocytes are incapable of digesting collagen scaffolds when the basal keratinocytes are grown on a collagen scaffold in vitro.

7b. Inhibiting Collagenase Activity Using Calcium Induction

The collagenase activity of basal keratinocytes may be inhibited by altering the cells' culture conditions before the cells are seeded on a collagen scaffold (e.g. Spongostan™). In one embodiment, this is accomplished by exposing isolated basal epithelium cells to different media formulations. This process begins by culturing basal epithelium cells in PCT medium (Progenitor Cell Targeting Medium) (Cat#CnT-07, Chemicon) until the cells have reached a suitable level of confluency. By way of example only, confluency may reach between 70-90%. The cells are then cultured in calcium-free Epidermal Keratinocyte Medium (Cat#CnT-02, Chemicon), after which this medium formulation is supplemented with 1.2 mm calcium. After culturing in calcium supplemented medium, the cells show reduced collagenase activity and decreased ability to digest collagen scaffolds.

7c. Inhibiting Collagenase Activity Using Fibroblast-Conditioned Medium

Fibroblast-conditioned medium provides another means for inhibiting the collagenase expression (i.e. activity) of precursor kerationcytes. In general, this is accomplished by culturing basal keratinocytes from the basal epithelium in fibroblast-conditioned medium. Fibroblast-conditioned medium is well known in the art and instructions for producing it are readily available (see e.g. van Roozendaal et al. Int J. Cancer. 1996 Jan. 3; 65(1):120-5 and Buffey et al. Br J. Dermatol. 1994 December; 131(6):836-42). The duration of culture in fibroblast-conditioned medium may vary, and by way of example only, this period may be between about 3 and 5 days.

EXAMPLE 1

Equipment and Materials

Laminar flow hood
CO$_2$ incubator
Inverted microscope
PCT medium (Progenitor Cell Targeting Medium) (Cat#CnT-07, Chemicon)
Epidermal Keratinocyte Medium (Cat#CnT-02, Chemicon)
1M Calcium Chloride (CaCl2) (Cat#SH30289.01, Lot #NAQS24 656, HyClone)
Dermal Fibroblasts Medium (Cat#CnT-05, Chemicon)
PBS (Ca-free) (Lot#1332722, Cat #20012, Gibco)
Hank's solution Ca-free (Lot#1326012, Cat#14170, Gibco)
0.25% Trypsin-0.5 mM EDTA solution (Lot#1329679, Cat#252000-106 Invitrogen. Inc)
Trypan blue solution (Lot #36K2353, Cat. T8154, Sigma)
12, 24-well plates
Culture flask, 25 cm$^2$
15, 50 ml sterile plastic tubes
Spongostan (Johnson@Johnson)
Live/Dead Viability/Cytotoxicity Kit:
Calcein AM (component A), two vials, 40 µl each, 4 mM in anhydrous DMSO,
Ethidium Homodimer—1 (component B), two vials, 200 µl each, 2 mM in DMSO/H2O 1:4 (v/v) (Molecular Probes Invitrogen detection technologies).

EXAMPLE 2

Primary Cell Culture

An abdominal skin biopsy from a 44-45 year old Hispanic female was washed 10 times in 100 ml of Gentamicin solution in calcium-free PBS. The washed skin was trimmed to remove the fat and to expose the dermal layer. The trimmed skin was cut with scissors on pieces 3 mm thick and 3 cm long. The pieces were washed 3 times in 30 ml of Gentamicin solution in Ca-free PBS. The washed pieces were incubated in 0.125% Dispase solution in Ca-free PBS for 18 hr at +4 C. Following incubation, the epidermis was peeled off by forceps and placed in calcium-free PBS. The isolated epidermis was digested in 0.125% Trypsin-0.53 mM EDTA solution for 3 min in the water bath at 37 C. The digestion was stopped with ×2 amount of 1% human albumin solution in RPMI-1640 culture medium. The cell suspension was filtered through 200µ nylon mesh, centrifuged, resuspended in calcium-free Hank's solution and the cell count was determined.

The cells were centrifuged again, resuspended in Keratinocyte Precursor Cell Targeted (PCT) serum-free medium (Chemicon Int.). The cell concentration was adjusted to $2 \times 10^5$ cells/ml and the cells were seeded in culture flasks (uncoated). The remaining dermal layer was digested in 0.2% Collagenase I—Hank's solution for 1-2 hr at 37 C in the water bath. The cell suspension was filtered through 200µ nylon mesh, centrifuged, resuspended in calcium-free Hank's solution and the cell count was determined. The cells were centrifuged again and resuspended in Dermal Fibroblast medium (Chemicon Int.). The cell concentration was adjusted to $2 \times 10^5$ cells/ml and the cells were seeded in culture flasks.

EXAMPLE 3

Preparation of Spongostan for Fibroblast Seeding

1. Cut a circle from Spongostan film 2.5 cm in diameter.
2. Put circle of Spongostan into a well of the 24-well plate.
3. Add 500 µl of Dermal Fibroblasts Medium (Cat#CnT-05, Chemicon) to well with Spongostan to prepare for cell culturing in CnT-05 medium
4. Place 24-well plate in a 37 C, CO2 incubator for 30 minutes.
5. Remove 24-well plate from an incubator.
6. Remove the medium from the well.
7. Add 500 µl of CnT-05 medium to a well with Spongostan.
8. Place 24-well plate in a 37 C, CO2 incubator for 30 minutes
9. Repeat 3-8 steps (washing) 2 times.

EXAMPLE 4

Harvesting and Seeding Fibroblasts

The medium was removed and the flasks were washed once with 5 ml of PBS solution. 2 ml of 0.25% Trypsin-0.5 mM EDTA solution was added to flasks and they were incubated for 5 minutes in a 37 C, CO2 incubator. When approximately 90% of fibroblasts were dislodged, the trypsin reaction was stopped by adding 3 ml of CnT-05 medium. The cells were spun at 1,500 rpm for 5 minutes. The cell pellet was resuspended in 10 ml of Hank's solution and the cells were counted in hemocytometer. 1.4 ml of cell suspension cells were spun down at 1,500 rpm for 5 minutes. The cell pellet was gently resuspended in 2 ml of CnT-05 medium and the cells were seeded in to a well of 24-well plate on Spongostan at a cell concentration of $5 \times 10^4$ per $cm^2$ or $4 \times 10^5$ cells/ml and in control wells using 250 µl of CnT-05 medium containing $1 \times 10^5$ cells/ml. Spongostan with seeded fibroblasts was washed 3 times using PCT medium to equilibrate PH.

EXAMPLE 5

Preparation of Spongostan for Keratinocyte Seeding

1. Cut a circle from Spongostan film 2.5 cm in diameter.
2. Put circle of Spongostan into a well of the 24-well plate.
3. Add 500 µl of PCT medium well with Spongostan to prepare for cell culturing in Progenitor cell targeting medium (Cat#Cnt-07, Chemicon).
4. Place 24-well plate in a 37 C, CO2 incubator for 30 minutes.
5. Remove 24-well plate from an incubator.
6. Remove the medium from the well.
7. Add 500 µl of PCT to a well with Spongostan.
8. Place 24-well plate in a 37 C, CO2 incubator for 30 minutes
9. Repeat 3-8 steps (washing) 2 times.

EXAMPLE 6

Harvesting and Seeding Keratinocytes

The medium was removed and the flasks were washed once with 5 ml of PBS solution. 2 ml of o 0.25% Trypsin-0.5 mM EDTA solution was added to flasks and they were incubated for 5 minutes in a 37 C, CO2 incubator. The trypsin reaction was stopped by adding 3 ml of Albumin Stopping medium. The cells were spun at 1,500 rpm for 5 minutes. The cell pellet was resuspended in 5 ml of Hank's solution and the cells were counted in hemocytometer. 2.6 ml of cell suspension cells were spun down at 1,500 rpm for 5 minutes. The cell pellet was gently resuspended in 2 ml PCT the cells were seeded in to a well of 24-well plate on Spongostan at $4 \times 10^5$ cells/ml ($5 \times 10^4$ cells/$cm^2$) in 250 µl of PCT medium. The basal-keratinocyte-seeded scaffold was then overlaid with the fibroblast-seeded scaffolds of Example 4 in a sandwich configuration (i.e. the seeded surfaces were contacted with one another). Control wells were seeded with keratinocytes alone, or on Spongostan scaffolds.

EXAMPLE 7

Cell Visualization

For cell visualization on the spongostan a color fluorescence cell viability assay using Live/Dead Viability/Cytotoxicity Kit for mammalian cells was performed:

1. The Live reagent stock solutions was removed from freezer and warmed to room temperature.
2. 10 µl of 2 mM EthD-1 stock solution (component B) was added to 0.5 ml of Hank's solution (calcium-free) solution
3. 2.5 µl of the of the supplied 4 mM calcein AM stock solution (component A) was added to the 1 ml of EthD-1-Hank's solution.
4. The resulting solution was pipetted to ensure thorough mixing.
5. The cells were incubated for 20 minutes in an 37 C, 5% CO2 incubator.
6. The labeled cells were viewed under the fluorescence inverted microscope. A lot of green (live) cells and epithelium colonies were seen on Spongostan.

EXAMPLE 8

Results

Fibroblasts grew well in culture when seeded with and without Spongostan. No Spongostan lysis occurred when the scaffolds were seeded with fibroblasts alone (FIG. 2).

FIG. 3 summarizes the results from seeding basal keratinocytes on Spongostan alone, and on Spongostan in a layered, sandwich configuration with fibroblasts. Visual inspection of the culture wells showed that Spongostan scaffolds seeded with basal keratinocytes alone were digested. In contrast, there was no digestion of the scaffold when the basal keratinocytes and fibroblasts were cultured in a sandwich configuration.

Figure 6:

FIGS. 4 and 6 are micrographs of the basal keratinocyte seeded-scaffold after rescue from the sandwich configuration. The image demonstrates the Spongostan scaffold was preserved as collagen fibers appear in the image. The image also shows the basal keratinocytes proliferated in culture.

Figure 5:
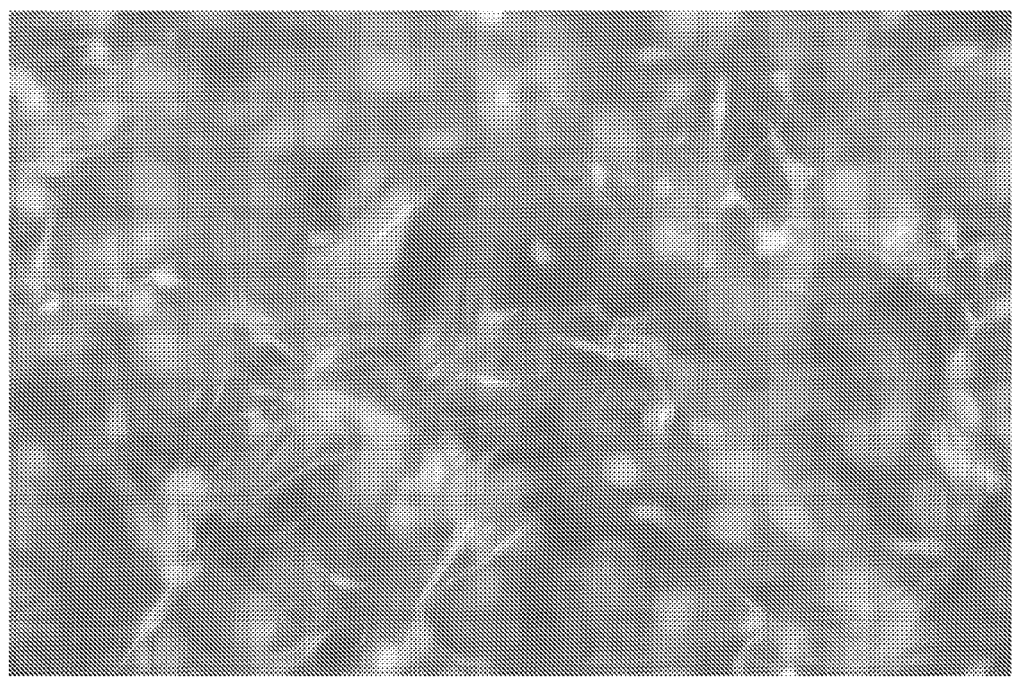
FIGS. 5 and 7 are images of a fibroblast-seeded cell scaffold that was rescued after culture in a sandwich configuration with a keratinocyte-seeded scaffold.
Figure 7:

FIGS. 5 and 7 are images of fibroblast-seeded scaffolds rescued after culture with a basal Keratinocyte-seeded scaffold. The scaffold fibers are clearly present as are the fibroblasts permeating the scaffold.

We claim:
1. A cellular scaffold arrangement comprising:
   a first collagen cell scaffold having a first surface and a second surface wherein said second surface of said first cell scaffold is seeded with mesenchymal cells; and
   a second collagen cell scaffold having a first surface and a second surface wherein said first surface of said second cell scaffold is seeded with ectodermal cells;
   wherein said second surface of said first scaffold is in contact with said first surface of said second scaffold;
   wherein said second cell scaffold has the consistency of a sponge.
2. The cellular scaffold-of claim 1, wherein said first cell scaffold has a consistency selected from a sponge, a membrane, a gel, and combinations thereof.
3. The cellular scaffold of claim 1, wherein said mesenchymal cells are derived from at least one of umbilical cord blood, placenta, bone marrow and peripheral blood.
4. The cellular scaffold of claim 1, wherein said mesenchymal cells comprise fibroblasts.
5. The cellular scaffold of claim 1, wherein said ectodermal cells comprise precursor keratinocytes.
6. The cellular scaffold of claim 1, wherein said ectodermal cells are derived from basal keratinocytes.
7. The cellular scaffold of claim 5, wherein said precursor keratinocytes are inhibited in collagenase production.

8. A layered cellular scaffold comprising:
a first collagen cellular scaffold having a contacting surface that is seeded with a plurality of cells comprising ectodermal cells;
a second collagen cellular scaffold having a contacting surface that is seeded with mesenchymal cells; and
a scaffold interface wherein said first scaffold contacting surface substantially contacts said second scaffold contacting surface;
wherein said first cellular scaffold has the consistency of a sponge.

9. The layered cellular scaffold of claim 8, wherein said second cellular scaffold has a consistency selected from a sponge, a membrane, a gel, and combinations thereof.

10. The layered cellular scaffold of claim 8, wherein said mesenchymal cells are derived from at least one of umbilical cord blood, placenta, bone marrow and peripheral blood.

11. The layered cellular scaffold of claim 8, wherein said mesenchymal cells comprise fibroblasts.

12. The layered cellular scaffold of claim 8, wherein said ectodermal cells comprise precursor keratinocytes.

13. The layered cellular scaffold of claim 8, wherein said ectodermal cells are derived from basal keratinocytes.

14. The layered cellular scaffold of claim 12, wherein said precursor keratinocytes are inhibited in collagenase production.

15. A method of making a layered cellular scaffold comprising:
providing a first cell substrate having a first surface and a second surface;
seeding said second surface of said first cell substrate with ectodermal cells;
providing a second cell substrate having a first surface and a second surface;
seeding said first surface of said second cell substrate with mesenchymal cells; and
contacting said second surface of said first cell substrate with said first surface of said second cell substrate thereby producing said layered cellular scaffold;
wherein said first and second cell substrates comprise collagen; and
wherein said first cell substrate has the consistency of a sponge.

16. The method of claim 15, wherein said second cell substrate has a consistency selected from a sponge, a membrane, a gel, and combinations thereof.

17. The method of claim 15, wherein said mesenchymal cells are derived from at least one of umbilical cord blood, placenta, bone marrow and peripheral blood.

18. The method of claim 15, wherein said mesenchymal cells are fibroblasts.

19. The method of claim 15, wherein said ectodermal cells are precursor keratinocytes.

20. The method of claim 15, wherein said ectodermal cells are derived from basal keratinocytes.

21. The method of claim 19, wherein said precursor keratinocytes are inhibited in collagenase production.

22. A method for making a layered cellular scaffold comprising:
providing a first cell scaffold and a second cell scaffold;
seeding a surface of said first cell scaffold with mesenchymal cells;
seeding a surface of said second cell scaffold with ectodermal cells; and
substantially joining said seeded surfaces to create said layered cellular scaffold;
wherein said first and said second cell scaffolds comprise collagen; and
wherein said second cell scaffold has the consistency of a sponge.

23. The method of claim 22, wherein said first cell scaffold has a consistency selected from a sponge, a membrane, a gel, and combinations thereof.

24. The method of claim 22, wherein said mesenchymal cells are derived from at least one of umbilical cord blood, placenta, bone marrow and peripheral blood.

25. The method of claim 22, wherein said mesenchymal cells are fibroblasts.

26. The method of claim 22, wherein said ectodermal cells are precursor keratinocytes.

27. The method of claim 22, wherein said ectodermal cells are derived from basal keratinocytes.

28. The method of claim 26, wherein said precursor keratinocytes are inhibited in collagenase production.

* * * * *